US010557807B2

(12) United States Patent
Ros et al.

(10) Patent No.: US 10,557,807 B2
(45) Date of Patent: Feb. 11, 2020

(54) 3D PRINTED MICROFLUIDIC MIXERS AND NOZZLES FOR CRYSTALLOGRAPHY

(71) Applicant: ARIZONA BOARD OF REGENTS ON BEHALF OF ARIZONA STATE UNIVERSITY, Scottsdale, AZ (US)

(72) Inventors: Alexandra Ros, Phoenix, AZ (US); Gerrit Brehm, Göttingen (DE); Garrett Nelson, Mesa, AZ (US); John Spence, Tempe, AZ (US); Uwe Weierstall, Phoenix, AZ (US); Austin Echelmeier, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 16/328,262

(22) PCT Filed: May 22, 2018

(86) PCT No.: PCT/US2018/033944
§ 371 (c)(1),
(2) Date: Feb. 25, 2019

(87) PCT Pub. No.: WO2018/217793
PCT Pub. Date: Nov. 29, 2018

(65) Prior Publication Data
US 2019/0178822 A1    Jun. 13, 2019

Related U.S. Application Data

(60) Provisional application No. 62/509,515, filed on May 22, 2017.

(51) Int. Cl.
*G01N 23/2005*    (2018.01)
*B01F 13/00*    (2006.01)
(Continued)

(52) U.S. Cl.
CPC ..... *G01N 23/2005* (2013.01); *B01F 13/0062* (2013.01); *B01L 3/502715* (2013.01);
(Continued)

(58) Field of Classification Search
CPC ......... G01N 23/2005; G01N 23/20025; G01N 2223/602; G01N 2223/604; B33Y 80/00;
(Continued)

(56) References Cited

U.S. PATENT DOCUMENTS 6,822,180 B2    11/2004  Fujii et al.
7,341,211 B2     3/2008  Ganan Calvo et al.
(Continued)

FOREIGN PATENT DOCUMENTS

WO    2013075081 A2    5/2013
WO    2016044545 A1    3/2016
(Continued)

OTHER PUBLICATIONS

International Search Report and Written Opinion received in International Application No. PCT/US2018/033944, dated Sep. 26, 2018 (9 pages).
(Continued)

*Primary Examiner* — Taeho Jo
(74) *Attorney, Agent, or Firm* — Michael Best & Friedrich LLP

(57) ABSTRACT

A 3D printed hybrid nozzle device combining a microfluidic mixer with a liquid jet injector that addresses the bottleneck of investigating substrate-initiated biological reaction paths employing serial crystallography with XFELs. The hybrid nozzle provides for injecting aqueous protein crystal jets after fast mixing (<5 ms), reaching reaction time points (e.g., about 10 ms to about 150 ms) suitable to resolve enzyme kinetics.

19 Claims, 20 Drawing Sheets

(51) Int. Cl.
 *B33Y 80/00* (2015.01)
 *G01N 23/20025* (2018.01)
 *B01L 3/00* (2006.01)

(52) U.S. Cl.
 CPC ........ *B33Y 80/00* (2014.12); *G01N 23/20025* (2013.01); *B01F 2215/0037* (2013.01); *B01L 2300/0867* (2013.01); *G01N 2223/602* (2013.01)

(58) Field of Classification Search
 CPC .......... B01F 13/0062; B01F 2215/0037; B01L 3/5027; B01L 3/502715; B01L 2300/0867
 See application file for complete search history.

(56) References Cited

U.S. PATENT DOCUMENTS

| | | | |
|---|---|---|---|
| 7,584,857 B2 | 9/2009 | Böhm et al. | |
| 8,272,576 B2 | 9/2012 | Doak et al. | |
| 8,658,367 B2 | 2/2014 | Quake et al. | |
| 8,827,548 B2 | 9/2014 | Roukes et al. | |
| 9,192,944 B2 | 11/2015 | Ros et al. | |
| 9,227,200 B2 | 1/2016 | Chiou et al. | |
| 9,387,488 B2 | 7/2016 | Chou et al. | |
| 9,446,360 B2 | 9/2016 | Mazutis | |
| 9,643,136 B2 | 5/2017 | Hansen et al. | |
| 10,166,542 B2 | 1/2019 | Ros et al. | |
| 10,413,920 B2 | 9/2019 | Doak et al. | |
| 2007/0080062 A1 | 4/2007 | Harnett et al. | |
| 2007/0228049 A1* | 10/2007 | Nordmeyer | B01L 9/065 220/560.07 |
| 2008/0105565 A1 | 5/2008 | Davalos et al. | |
| 2010/0163116 A1 | 7/2010 | Fang et al. | |
| 2010/0224255 A1 | 9/2010 | Mathies et al. | |
| 2010/0224493 A1 | 9/2010 | Davalos et al. | |
| 2010/0303687 A1 | 12/2010 | Blaga et al. | |
| 2012/0021523 A1 | 1/2012 | Fowler et al. | |
| 2012/0085649 A1 | 4/2012 | Sano et al. | |
| 2012/0266986 A1 | 10/2012 | Wimberger-Friedl et al. | |
| 2013/0032235 A1 | 2/2013 | Johnstone et al. | |
| 2013/0295653 A1 | 11/2013 | Quake et al. | |
| 2013/0308756 A1* | 11/2013 | Bogan | H01J 49/0431 378/86 |
| 2013/0313336 A1 | 11/2013 | Doak et al. | |
| 2014/0038279 A1 | 2/2014 | Ingber et al. | |
| 2014/0091012 A1* | 4/2014 | Ros | B03C 5/005 209/129 |
| 2014/0263693 A1* | 9/2014 | Doak | B05B 7/064 239/1 |
| 2014/0295572 A1 | 10/2014 | Fraden et al. | |
| 2015/0087559 A1 | 3/2015 | Putnam et al. | |
| 2016/0051995 A1* | 2/2016 | Weierstall | B05B 7/08 239/8 |
| 2016/0151784 A1 | 6/2016 | Chiou et al. | |
| 2016/0341675 A1* | 11/2016 | Doak | G01N 23/20008 |
| 2016/0370306 A1* | 12/2016 | Conrad | G01N 23/2005 |
| 2017/0274380 A1* | 9/2017 | Weierstall | B01F 5/045 |
| 2018/0154380 A1* | 6/2018 | Doak | B05B 7/0475 |
| 2019/0134631 A1 | 5/2019 | Ros et al. | |
| 2019/0184395 A1 | 6/2019 | Ros et al. | |
| 2019/0224689 A1 | 7/2019 | Ros et al. | |

FOREIGN PATENT DOCUMENTS

| | | |
|---|---|---|
| WO | 2016164562 A1 | 10/2016 |
| WO | 2017003725 A1 | 1/2017 |
| WO | 2018013685 A1 | 1/2018 |
| WO | 2018217831 A1 | 11/2018 |

OTHER PUBLICATIONS

Akthakul A. et al., "Size fractionation of metal nanoparticles by membrane filtration", Advanced Materials, vol. 17, Issue 5, pp. 532-535 (2005).
Almen M.S. et al., "Mapping the human membrane proteome: a majority of the human membrane proteins can be classified according to function and evolutionary origin", BMC Biology, vol. 7, Issue 1, pp. 50 (2009).
Bhattacharya S. et al., "Insulator-based dielectrophoretic single particle and single cancer cell trapping", Electrophoresis, vol. 32, Issue 18, pp. 2550-2558 (2011).
Bligh M. et al., "Sorting microparticles into lateral streams using a two-phase rectangular electrokinetic array", Journal of Micromechanics and Microengineering, vol. 18, Issue 4, pp. 045002 (2008).
Boekema E.J. et al., "Evidence for a trimeric organization of the photosystem I complex from the thermophilic cyanobacterium *Synechococcus* sp.", FEBS Letters, vol. 217, Issue 2, pp. 283-286 (1987).
Bogunovic et al., Particle sorting by a structured microfluidic ratchet device with tunable selectivity: theory and experiment. Soft Matter 2012, 8 (14), 3900-3907.
Boutet S. et al., "High-Resolution Protein Structure Determination by Serial Femtosecond Crystallography", Science, vol. 337, Issue 6092, pp. 362-364 (2012).
Calzolai L. et al., "Separation and characterization of gold nanoparticle mixtures by flow-field-flow fractionation", Journal of Chromatography A, vol. 1218, Issue 27, pp. 4234-4239 (2011).
Cesaro-Tadic et al., High-sensitivity miniaturized immunoassays for tumor necrosis factor a using microlluidic systems. Lab on a Chip 2004, 4 (6), 563-569.
Chapman H. N. et al., "Femtosecond X-ray protein nanocrystallography", Nature-London, vol. 470, Issue 7332, pp. 73-77 (2011).
Chapman H.N., "X-ray imaging beyond the limits", Nature Materials, vol. 8, Issue 4, pp. 299-301 (2009).
Chen G. et al., "High-Purity Separation of Gold Nanoparticle Dimers and Trimers", Journal of the American Chemical Society, vol. 131, Issue 12, pp. 4218-4219 (2009).
Cheng I.F. et al., "A continuous high-throughput bioparticle sorter based on 3D traveling-wave dielectrophoresis", Lab on a chip, vol. 9, Issue 22. pp. 3193-3201 (2009).
Chinen et al., Nanoparticle Probes for the Detection of Cancer Biomarkers, Cells, and Tissues by Fluorescence. Chemical Reviews 2015, 115 (19), 10530-10574.
Chung et al., Ultrastructural changes of mitochondria in the skeletal muscle of patients with amyotrophic lateral sclerosis. Ultrastruct Pathol 2002, 26 (1), 3-7.
Cordelières, "Manual Tracking," ImageJ plugin, 2005, <https://imagej-nihgov.ezproxy1.lib.asu.edu/ij/plugins/track/track.html> 3 pages.
Cummings E.B. et al., "Dielectrophoresis in Microchips Containing Arrays of Insulating Posts: Theoretical and Experimental Results", Analytical Chemistry, vol. 75, Issue 18, pp. 4724-4731 (2003).
Davalos et al., "Performance impact of dynamic surface coatings on polymeric insulator-based dielectrophoretic particle separators," Anal. Bioanal. Chem. 2008, 390, 847-855.
Dertinger S.K.W. et al., "Generation of Gradients Having Complex Shapes Using Microfluidic Networks", Anal. Chem., 73, 1240-1246 (2001).
Doak R.B. et al., "Microscopic linear liquid streams in vacuum: Injection of solvated biological samples into X-ray free electron lasers", AIP Conference Proceedings, vol. 1501, pp. 1314-1323 (2012).
Drews et al., Ratcheted electrophoresis for rapid particle transport Lab on a Chip 2013, 13 (22), 4295-4298.
Duffy et al., "Determination of Properties of Individual Liposomes by Capillary Electrophoresis with Postcolumn Laser-Induced Fluorescence Detection," Anal. Chem. 2001, 73, 1855-1861.
Eguchi et al., Giant mitochondria in acute lymphocytic leukemia. Exp Mol Pathol 1987, 47(1), 69-75.
Fernández-Vizarra et al., Isolation of biogenetically competent mitochondria from mammalian tissues and cultured cells. Methods 2002, 26 (4), 292-297.
Fiedler S. et al., "Dielectrophoretic Sorting of Particles and Cells in a Microsystem", Analytical Chemistry, vol. 70, Issue 9, pp. 1909-1915 (1998).
Fromme P et al., "Improved isolation and crystallization of Photosystem I for structural analysis", Biochimica et Biophysica Acta, vol. 1365, Issue 1-2, pp. 175-184 (1998).

(56) References Cited

OTHER PUBLICATIONS

Gan et al., "Six Helix Bundle and Triangle DNA Origami Insulator-Based Dielectrophoresis," Anal. Chem. 2013, 85, 11427-11434.
Gascoyne P.R. et al., "Particle separation by dielectrophoresis", Electrophoresis, vol. 23, Issue 13, pp. 1973-1983 (2002).
Gerion D. et al., "Sorting Fluorescent Nanocrystals with DNA", Journal of the American Chemical Society, vol. 124, Issue 24, pp. 7070-7074 (2002).
Giddings, "Unified Separation Science," Wiley ; New York 1991.
Gonzalez et al., Gonzalez, C. F.; Remcho, V. T., Fabrication and evaluation of a ratchet type dielectrophoretic device for particle analysis. Journal of Chromatography A 2009, 1216 (52), 9063-9070.
Gorre-Talini et al., Dielectrophoretic ratchets. Chaos 1998, 8(3), 650-656.
Green N.G. et al., "Dielectrophoresis of Submicrometer Latex Spheres. 1. Experimental Results", Journal of Physical Chemistry B, vol. 103, Issue 1, pp. 41-50 (1999).
Haenggi et al., Artificial Brownian motors: Controlling transport on the nanoscale. Reviews of Modern Physics 2009, 81 (1), 387-442.
Heffner et al., The early effects of ischemia upon skeletal muscle mitochondria. J Neurol Sci 1978, 38 (3), 295-315.
Hellmich W. et al., "Poly(oxyethylene) Based Surface Coatings for Poly(dimethylsiloxane) Microchannels", Langmuir, vol. 21, Issue 16, pp. 7551-7557 (2005).
Holmes D. et al., "On-chip high-speed sorting of micron-sized particles for high-throughput analysis", IEE proceedings. Nanobiotechnology, vol. 152, Issue 4, pp. 129-135 (2005).
Holzel et al., "Trapping Single Molecules by Dielectrophoresis," Phys. Rev. Lett. 2005, 95, 128102.
Hornig-Do et al., "Isolation of functional pure mitochondria by superparamagnetic microbeads," Anal. Biochem. 2009, 389, 1-5.
Huang et al., "Current-monitoring method for measuring the electroosmotic flow rate in capillary zone electrophoresis," Anal. Chem. 1988, 60, 1837-1838.
Hunter M.S. et al., "Toward structure determination using membrane-protein nanocrystals and microcrystals", Methods, vol. 55, Issue 4, pp. 387-404 (2011).
Hunter M.S. et al., "X-ray Diffraction from Membrane Protein Nanocrystals", Biophysical Journal, vol. 100, Issue 1, pp. 198-206 (2011).
International Preliminary Report on Patentability for Application No. PCT/US2017/041708 dated Jan. 24, 2019, 8 pages.
International Search Report and Written Opinion for Application No. PCT/US2015/050616 dated Jan. 18, 2016, 11 pages.
International Search Report and Written Opinion for Application No. PCT/US2017/041708 dated Oct. 23, 2017, 9 pages.
International Search Report and Written Opinion for Application No. PCT/US2018/033944 dated Sep. 26, 2018, 14 pages.
International Search Report and Written Opinion for Application No. PCT/US2018/033989 dated Jul. 20, 2018, 13 pages.
Jeon N.L. et al., "Generation of Solution and Surface Gradients Using Microfluidic Systems", Langmuir, 16, 8311-8316 (2000).
Jones et al., "Continuous Separation of DNA Molecules by Size Using Insulator-Based Dielectrophoresis," Anal. Chem. 2017, 89, 1531-1539.
Jordan P. et al., "Three-dimensional structure of cyanobacterial photosystem I at 2.5 A resolution", Nature, vol. 411, Jun. 21, pp. 909-917 (2001).
Srivastava S.K. et al., "A continuous DC-insulator dielectrophoretic sorter of microparticles", Journal of chromatography. A, vol. 1218, Issue 13, pp. 1780-1789 (2011).
Srivastava S.K. et al., "DC insulator dielectrophoretic applications in microdevice technology: a review", Analytical and Bioanalytical Chemistry, vol. 399, Issue 1, pp. 301-321 (2011).
Srivastava S.K. et al., "Direct current insulator-based dielectrophoretic characterization of erythrocytes: ABO-Rh human blood typing", Electrophoresis, vol. 32, Issue 18, pp. 2530-2540 (2011).
Sturm et al., Ratchets in hydrodynamic flow: more than waterwheels. Interface Focus 2014, 4 (6) 9 pages.

Thoenes et al., On matrix-rich giant mitochondria. Electron microscopic observations on tubular epithelium of the human kidney in the nephrotic syndrome. Z Zellforsch Mikrosk Anat 1966, 75 (2), 422-33.
Unger et al., "Monolithic microfabricated valves and pumps by multilayer soft lithography," Science, 288, 113-16 (2000).
Viefhues M. et al., "Physisorbed surface coatings for poly(dimethylsiloxane) and quartz microfluidic devices", Analytical and Bioanalytical Chemistry, vol. 401, Issue 7, pp. 2113-2122 (2011).
Wampler R.E et al., "Selective Detection of Protein Crystals by Second Harmonic Microscopy", Journal of the American Chemical Society, vol. 130, Issue 43, pp. 14076-14077 (2008).
Weierstall U. et al., "Injector for scattering measurements on fully solvated biospecies", Review of Scientific Instruments. vol. 83, Issue 3, pp. 035108 (2012).
Yamada et al. "Differential Permeabilization Effects of Ca2+ and Valinomycin on the Inner and Outer Mitochondrial Membranes as Revealed by Proteomics Analysis of Proteins Released from Mitochondria," Mol. Cell Proteomics, 2009, 8, 1265-1277.
Yang et al, "Toward Analysis of Proteins in Single Cells: A Quantitative Approach Employing Isobaric Tags with MALDI Mass Spectrometry Realized with a Microfluidic Platform," Anal. Chem. 2016, 88, 6672-6679.
Yang et al., High Speed Size Sorting of Subcellular Organelles by Flow Field-Flow Fractionation. Analytical Chemist 2015, 87 (12), 6342-6348.
Yang J. et al., "Size sorting of Au and Pt nanoparticles from arbitrary particle size distributions", Analytica Chimica Acta, vol. 546, Issue 2, pp. 133-138 (2005).
Yates et al, "Proteomics of organelles and large cellular structures," Nat. Rev. Mol. Cell Biol. 2005, 6, 702-714.
Zhu J. et al., Dielectrophoretic focusing of particles in a microchannel constriction using DC-biased AC flectric fields', Electrophoresis, vol. 30, Issue 15 pp. 2668-2675 (2009).
Jores K. et al., "Investigations on the structure of solid lipid nanoparticles (SLN) and oil-loaded solid lipid nanoparticles by photon correlation spectroscopy, field-flow fractionation and transmission electron microscopy", Journal of Controlled Release, vol. 95, Issue 2, pp. 217-227 (2004).
Kale et al., Continuous-flow dielectrophoretic trapping and patterning of colloidal particles in a ratchet microchannel. Journal of Micromechanics and Microengineering 2014, 24 (7) 6 pages.
Kang et al., Separation of mitochondria by flow field-flow fractionation for proteomic analysis. Analyst 2008, 133 (4), 505-515.
Kim et al., "Deterministic Ratchet for Sub-micrometer (Bio)particle Separation," Anal. Chem., 2018, 90 (7), pp. 4370-4379.
Kim et al., "Dynmanic Constriction Insulator-Based Dielectrophoresis for Particle Manipulation," 2016, 1 page.
Kissick D.J. et al., "Second-Order Nonlinear Optical Imaging of Chiral Crystals", Annual Review of Analytical Chemistry, vol. 4, pp. 419-437 (2011).
Kralj J.G. et al., "Continuous Dielectrophoretic Size-Based Particle Sorting", Analytical Chemistry, vol. 78, Issue 14, pp. 5019-5025 (2006).
Lapizco-Encinas B.H. et al., "Insulator-based dielectrophoresis for the selective concentration and separation of live bacteria in water", Electrophoresis, vol. 25, Issue 10-11, pp. 1695-1704 (2004).
Latham A.H. et al., "Capillary Magnetic Field Flow Fractionation and Analysis of Magnetic Nanoparticles", Analytical Chemistry, vol. 77, Issue 15, pp. 5055-5062 (2005).
Li N. et al., "Parallel mixing of photolithographically defined nanoliter volumes using elastomeric microvalve arrays", Electrophoresis, 26, 3758-3764 (2005).
Liao et al., "Nanoscale Molecular Traps and Dams for Ultrafast Protein Enrichment in High-Conductivity Buffers," J. Am. Chem. Soc. 2012, 134, 8742-8745.
Lin et al., Highly selective biomechanical separation of cancer cells from leukocytes using microfluidic ratchets and hydrodynamic concentrator. Biomicrofluidics 2013, 7 (3) ; 034114.
Loutherback et al., Deterministic Microfluidic Ratchet. Physical Review Letters 2009, 102, 045301.

(56) References Cited

OTHER PUBLICATIONS

Lundstrom K., "Structural genomics and drug discovery", Journal of Cellular and Molecular Medicine, vol. 11, Issue 2, pp. 224-238 (2007).
Luo et al., Insulator-based dielectrophoresis of mitochondria. Biomicrofluidics 2014, 8 (2), 021801.
Luo, J. H.; Muratore, K. A.; Arriaga, E. A.; Ros, A., Deterministic Absolute Negative Mobility for Micro- and Submicrometer Particles Induced in a Microfluidic Device. Analytical Chemistry 2016, 88 (11), 5920-5927.
Majewski P. et al., "Synthesis, Surface Modifications, and Size-Sorting of Mixed Nickel-Zinc Ferrite Colloidal Magnetic Nanoparticles", Chemistry: a European journal, vol. 14, Issue 26, pp. 7961-7968 (2008).
Marquet et al., Rectified motion of colloids in asymmetrically structured channels. Physical Review Letters 2002, 88 (16) 168301.
Martinez-Duarte R. et al., "Microfabrication technologies in dielectrophoresis applications—A review", Electrophoresis, vol. 33, Issue 21, pp. 3110-3132 (2012).
Martinez-Lopez et al., "Characterization of electrokinetic mobility of microparticles in order to improve dielectrophoretic concentration," Anal. Bioanal. Chem. 2009, 394, 293-302.
Matias et al., Giant mitochondria and intramitochondrial inclusions in benign thyroid lesions. Ultrastruct Pathol 1991, 15 (3), 221-9.
McFaul et al., Cell separation based on size and deformability using microfluidic funnel ratchets. Lab on a Chip 2012, 12 (13), 2369-2376.
Michelsen et al., Isolation of Subcellular Organelles and Structures. Methods in Enzymology 2009, 463, 305-28.
Morgan et al., Separation of submicron bioparticles by dielectrophoresis. Biophysical Journal 1999, 77 (1), 516-525.
Muller T. et al., "A 3-D microelectrode system for handling and caging single cells and particles", Biosensors & Bioelectronics, vol. 14, Issue 3, pp. 247-256 (1999).
Nakano A. et al., "Immunoglobulin G and bovine serum albumin streaming dielectrophoresis in a microfluidic device", Electrophoresis, vol. 32, Issue 17, pp. 2314-2322 (2011).
Nakano A. et al., "Tuning direct current streaming dielectrophoresis of proteins", Biomicrofluidics, vol. 6, Issue 3, pp. 34108 (2012).
Nakano et al., "Temporal and Spatial Temperature Measurement in Insulator-based Dielectrophoretic Devices," Analytical Chemistry (2014) 86, 6516-6524.
Nakano et al., Immunoglobulin G and bovine serum albumin streaming dielectrophoresis in a microfluidic device. Electrophoresis 2011, 32 (17), 2314-2322.
Navratil et al., Giant mitochondria do not fuse and exchange their contents with normal mitochondria. Exp Cell Res 2008, 314 (1), 164-72.
Nelson et al., "Three-dimensional-printed gas dynamic virtual nozzles for x-ray laser sample delivery". Optics Express, 2016, 24, 11515-11530.
Novak J P. et al., "Purification of Molecularly Bridged Metal Nanoparticle Arrays by Centrifugation and Size Exclusior Chromatography", Analytical Chemistry, vol. 73, Issue 23, pp. 5758-5761 (2001).
Ozuna-Chacon S. et al., "Performance characterization of an insulator-based dielectrophoretic microdevice", Electrophoresis, vol. 29, Issue 15, pp. 3115-3222 (2008).
Pamme N. et al., "Continuous sorting of magnetic cells via on-chip free-flow magnetophoresis", Lab on A Chip, vol. 6, Issue 8, pp. 974-980 (2006).
Pamme N. et al., "On-Chip Free-Flow Magnetophoresis: Continuous Flow Separation of Magnetic Particles and Agglomerates", Analytical Chemistry, vol. 76, Issue 24, pp. 7250-7256 (2004).
Papadimitriou et al., Giant mitochondria with paracrystalline inclusions in paraganglioma of the urinary bladder: correlation with mitochondrial abnormalities in paragangliomas of other sites. Ultrastruct Pathol 1994, 18 (6), 559-64.
Pethig, Review Article-Dielectrophoresis: Status of the theory, technology, and applications. Biomicrofluidics 2010, 4 (2) 022811-1-022811-35.
Pohl H.A. et al., "Di Electrophoresis of Cells", Biophysical Journal, vol. 11, pp. 711-727 (1971).
Pohl H.A. et al., "Dielectrophoretic Force", J Theor. Biol., vol. 37, pp. 1-13 (1972).
Pohl, Dielectrophoresis : The Behavior of Neutral Matter in Nonuniform Electric Fields. Cambridge ; New York : Cambridge University Press 1978.
Pommer M.S. et al., "Dielectrophoretic separation of platelets from diluted whole blood in microfluidic channels", Electrophoresis, vol. 29, Issue 6, pp. 1213-1218 (2008).
Redecke L. et al., "Natively Inhibited Trypanosoma brucei Cathepsin B Structure Determined by Using an X-ray Laser", Science, vol. 339, Issue 6116, pp. 227-230 (2013).
Regtmeier et al., "Dielectrophoretic manipulation of DNA: Separation and polarizability," A. Anal. Chem. 2007, 79, 3925-3932.
Regtmeier et al., Acceleration of absolute negative mobility. Journal of Separation Science 2007, 30 (10), 1461-1467.
Fromme P. et al., "Femtosecond nanocrystallography using X-ray lasers for membrane protein structure determination", Current Opinion in Structural Biology, vol. 21, Issue 4, pp. 509-516 (2011).
Safarik et al., Magnetic techniques for the isolation and purification of proteins and peptides. Biomagn Res Technol 2004, 2, 7, 18 pages.
Salomon S. et al., "A dielectrophoretic continuous flow sorterusing integrated microelectrodes coupled to a channel cnstriction", Electrophoresis, vol. 32, Issue 12, pp. 1508-1514 (2011).
Schubert W.D. et al., "Photosystem I of Synechococcus elongatus at 4 A Resolution: Comprehensive Structure Analysis", Journal of Molecular Biology, vol. 272, Issue 5, pp. 741-769 (1997).
Shafiq et al., Giant mitochondria in human muscle with inclusions. Arch Neurol 1967, 17 (6), 666-71.
Spence et al., (2012). "X-ray lasers for structural and dynamic biology". Reports on Progress in Physics, 75, 102601.

\* cited by examiner

| Crystal Suspension Flow Rate (μL/min) | Substrate Flow Rate, Each inlet (μL/min) | Time Point (ms) |
|---|---|---|
| 15 | 37.5 | 30 |
| 5 | 12.5 | 72 |
| 3.75 | 9.375 | 117 |
| 2.5 | 6.25 | 144 |

*FIG. 7*

Device Dimensions

| Dimension | Distance (mm) |
|---|---|
| Length | 2.3 |
| Width | 1.1 |
| Height | 0.6 |

Substrate Channel Dimensions

| Dimension | Distance (μm) |
|---|---|
| Inlet Diameter | 380 |
| Inner Channel Diameter | 275 |
| Length of Inner Channel | 1000 |
| Length of Taper | 300 |

Crystal Channel Dimensions

| Dimension | Distance (μm) |
|---|---|
| Inlet Diameter | 380 |
| Inner Channel Diameter | 75 |
| Length of Inner Channel | 500 |
| Length of Taper | 300 |
| Inner Channel Outer Diameter | 175 |

Outlet Channel Dimensions

| Dimension | Distance (μm) |
|---|---|
| Inner Channel Diameter | 275 |
| Length of Inner Channel | 500 |
| Outlet Diameter | 380 |
| Length of Taper | 300 |

FIG. 14

3D PRINTED MICROFLUIDIC MIXERS AND NOZZLES FOR CRYSTALLOGRAPHY

CROSS-REFERENCE TO RELATED APPLICATIONS

This application is a PCT international application and claims the benefit of U.S. Provisional Patent Application No. 62/509,515, filed on May 22, 2017, the entire contents of which are incorporated herein by reference.

STATEMENT REGARDING FEDERALLY SPONSORED RESEARCH OR DEVELOPMENT

This invention was made with government support under R01 GM095583 awarded by the National Institutes of Health and 1231306 awarded by the National Science Foundation. The government has certain rights in the invention.

BACKGROUND OF THE INVENTION

Resolving the structures of biological molecules has been boosted in the past few years through the use of technologies involving x-ray free electron lasers (XFELs) and crystallography experiments with these instruments. In particular, access to time-resolved structural information allowing a biochemical reaction path through crystallographic data analysis is regarded as a major future breakthrough with this technology.

In addition, time-resolved serial femtosecond X-ray crystallography (TR-SFX) studies have become possible elucidating insight in protein dynamics of important processes such as photosynthesis or antibiotic resistance. A major factor limiting TR-SFX experiments are reliable injection technologies compatible with the liquid jet injection methods employed for SFX which allow fast mixing and reach suitable reaction time points.

SUMMARY OF THE INVENTION

Serial femtosecond crystallography (SFX) with XFELs is mainly carried out with crystals suspended in an aqueous solution requiring the injection of a liquid jet of suspended crystals in a specially designed experimental chamber for exposure to an XFEL. To allow time resolved data acquisition, crystals need to be mixed rapidly and injected through a liquid jet. At least some such procedures would benefit from mixing times in the sub-microsecond range and reaction times vary depending on the biological reaction under study from a few milliseconds to several seconds or to a few minutes. In some embodiments, the invention provides a mechanism or device that allows substrate-enabled biochemical reactions to be studied by using microfluidic mixers coupled to a liquid jet injection in time scales needed for such biochemical reactions.

Accordingly, disclosed herein is the first 3D printed hybrid nozzle device injecting aqueous protein crystal jets after fast mixing (<5 ms), reaching reaction time points (e.g., about 10 ms to about 150 ms) suitable to resolve enzyme kinetics.

In some embodiments, the invention provides a 3D-printed, monolithic piece combining a microfluidic mixer with a liquid jet injector that addresses the bottleneck of investigating substrate-initiated biological reaction paths employing serial crystallography with XFELs. The 3D-printed piece, in some embodiments, is about 1-2 mm$^3$ and has microchannels and support structures embedded for liquid and gas flow. The mixing is carried out through a microfluidic mixer, allowing mixing by diffusion through hydrodynamic focusing. Mixing times can be adjusted by the employed liquid flow rates and geometric design. After mixing, liquids are further transported downstream to a region in which a gas-dynamic virtual nozzle is created forming a liquid jet for injection into an experimental chamber. In some embodiments, the 3D printed monolithic piece is further connected to capillary tubing allowing control of gas and liquid flow through external pumps. In some embodiments, the mixer can be decoupled from the nozzle when two individual pieces are printed which allows increasing reaction times up to several seconds or even minutes before crystallographic analysis.

In various embodiments, the invention allows time-resolved crystallography studies using jet injection techniques that are successful for serial crystallography with XFELs. The time scales of reaction times can be varied in a large range from several hundred microseconds to minutes when the mixer is decoupled from the nozzle. The combined piece where mixer and nozzle are printed in one monolithic structure allows easy adaptation to existing mounting techniques for jet nozzles and the application of the mixer in a vacuum chamber. The realization of a mixer/nozzle with 3D-printing is powerful as it allows reproducible production of the technology for a huge variety of XFEL experiments.

Additionally, the hybrid mixer/nozzle according to an embodiment of the invention, could be used for time resolved wide angle X-ray scattering (WAXS) or small angle X-ray scattering (SAXS) experiments at XFEL's. Reaction time points for WAXS may be less than 10 ms.

In one particular embodiment, the invention provides a system for conducting time-resolved serial femtosecond X-ray crystallography. The system comprises a hybrid nozzle including a microfluidic mixer integrally formed with a liquid jet injector. The hybrid nozzle further includes a housing, a first fluid inlet channel formed in the housing and configured to receive a substrate solution, a second fluid inlet channel formed in the housing and configured to receive a crystal suspension, and an outlet channel formed in the housing and coaxially formed with the second fluid inlet channel and in fluid communication with the first fluid inlet channel to provide mixing of the substrate solution and the crystal suspension within 1 ms to 5 ms. The mixture is transported to a chamber via the liquid jet injector for crystallographic analysis.

In another particular embodiment, the invention provides a system for conducting time-resolved serial femtosecond X-ray crystallography. The system comprises a microfluidic mixer including a housing, a first fluid inlet channel formed in the housing and configured to receive a substrate solution, a second fluid inlet channel formed in the housing and configured to receive a crystal suspension, and an outlet channel formed in the housing and configured to receive a first stream of the substrate solution and a second stream of the crystal suspension, wherein the second stream is coaxial with the first stream as the combined stream traverses along the outlet channel, and wherein the velocity of the second stream varies by 10% or less relative to the first stream.

Other aspects of the invention will become apparent by consideration of the detailed description and accompanying drawings.

BRIEF DESCRIPTION OF THE DRAWINGS

FIG. 7 is a table of flow rates and mixing times in the mixing example of FIG. 6.

FIG. 14 is a series of tables illustrating the dimensions of the coaxial mixer of FIG. 13A.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are hereby incorporated by reference in their entirety. The materials, methods, and examples disclosed herein are illustrative only and not intended to be limiting.

For the recitation of numeric ranges herein, each intervening number therebetween with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"About" is used synonymously herein with the term "approximately." Illustratively, the use of the term "about" indicates that values slightly outside the cited values, namely, plus or minus 10%. Such values are thus encompassed by the scope of the claims reciting the terms "about" and "approximately."

Figure 1A:
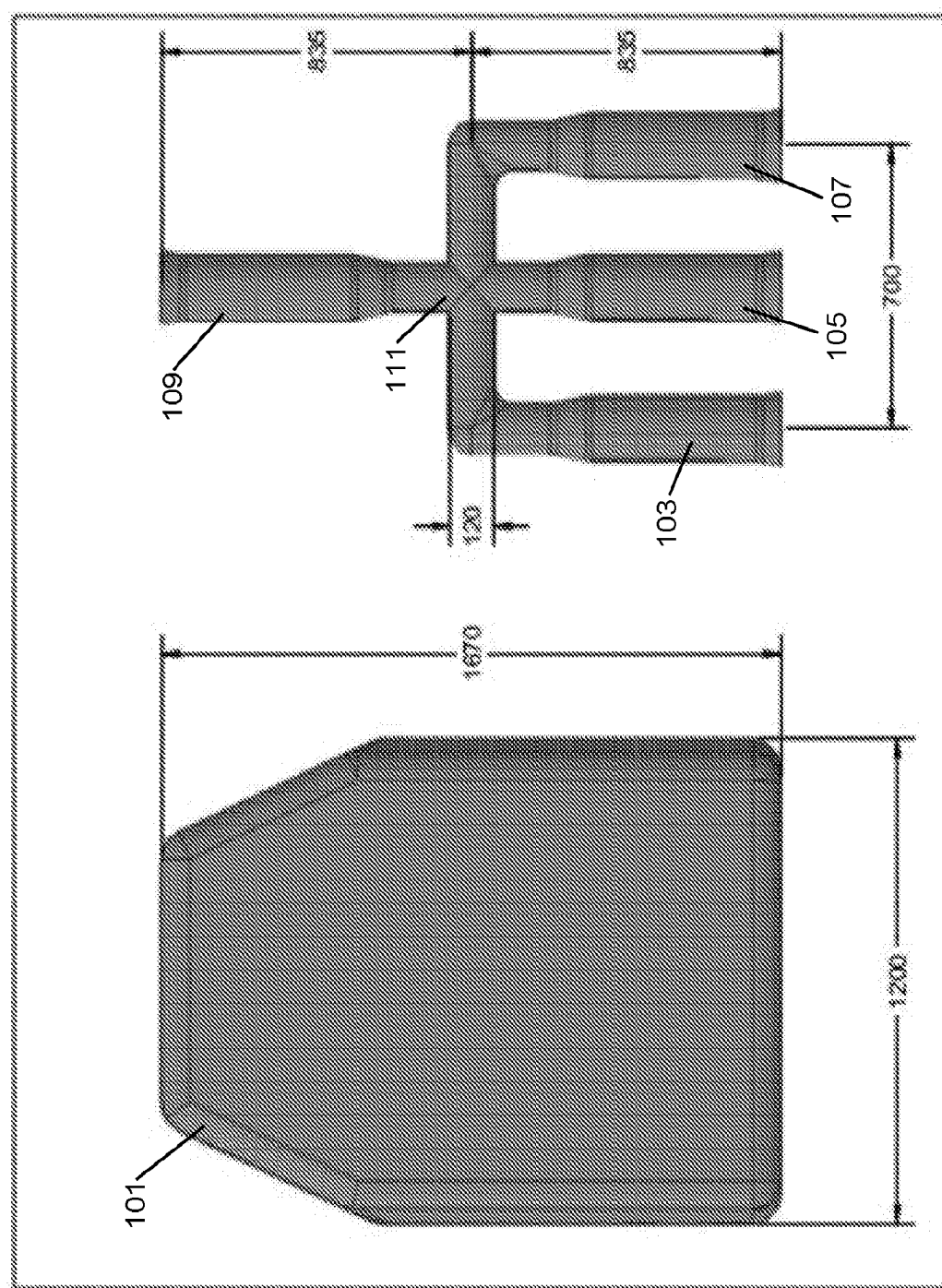
FIG. 1A is a top view of an exterior and the interior channels of a mixer component in accordance with one embodiment.
Figure 1B:
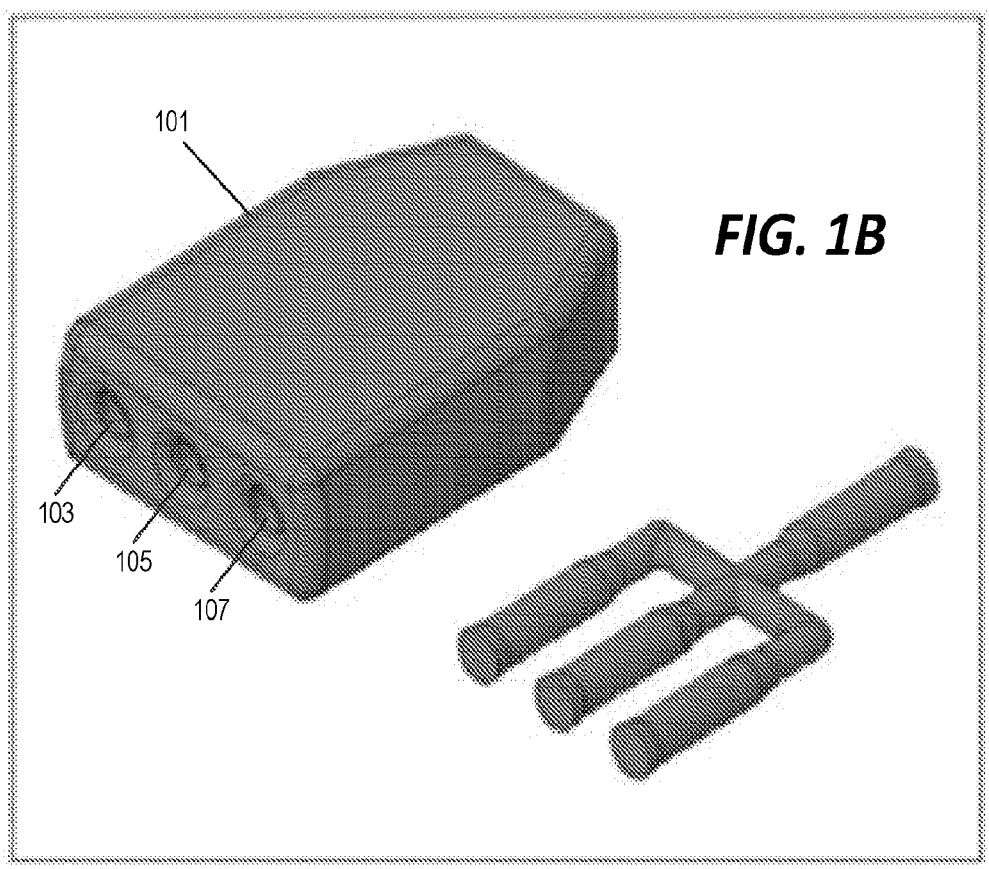
FIG. 1B is a perspective view of the exterior and the interior channels of the mixer component of FIG. 1A.
Figure 1C:
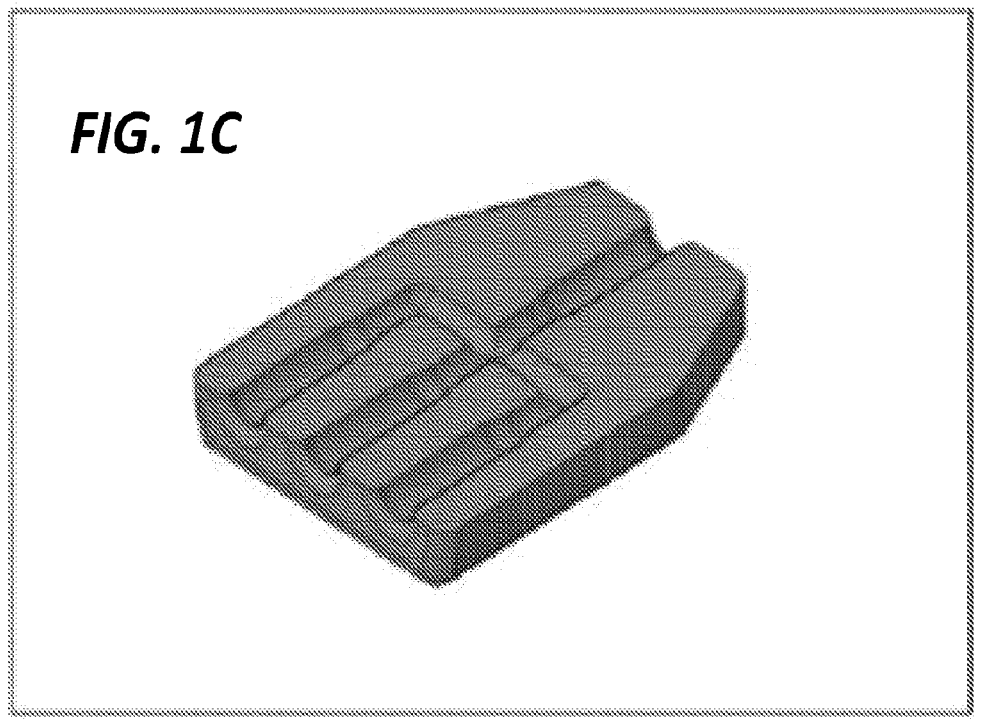
FIG. 1C is a perspective cut-away view of the mixer component of FIG. 1A showing the internal channels of the mixer component within the piece.

FIG. 1A illustrates an example of a mixer component generated by a 3D printing process. The image on the left side of FIG. 1A shows the exterior 101 of the mixer component and the image on the right side of FIG. 1A shows the internal channels of the 3D printed piece. The dimensions of the mixer component are illustrated in micrometers in FIG. 1A. FIG. 1B illustrates the mixer component of FIG. 1A in perspective view. The exterior 101 of the mixer component is shown on the left and the internal channels are illustrated on the right of FIG. 1B. FIG. 1C shows the same mixer component in cut-away to illustrate the placement of the internal channels within the exterior 101.

In the embodiment of FIG. 1A, the internal channels of the mixer component include three input channels 103, 105, 107 and one output channel 109. All four of the channels meet at a central point 111 where fluids and/or gases provided to the mixer through the input channels 103, 105, 107 are mixed before being expelled from the mixer component through the output channel 109. As shown in FIG. 1B, the input channels 103, 105, 107 are open to the outside of the exterior 101 for coupling with hoses from a pump/regulator and fluid/gas source. The output channel 109 is similarly open to the exterior for coupling to a hose.

Figure 2:
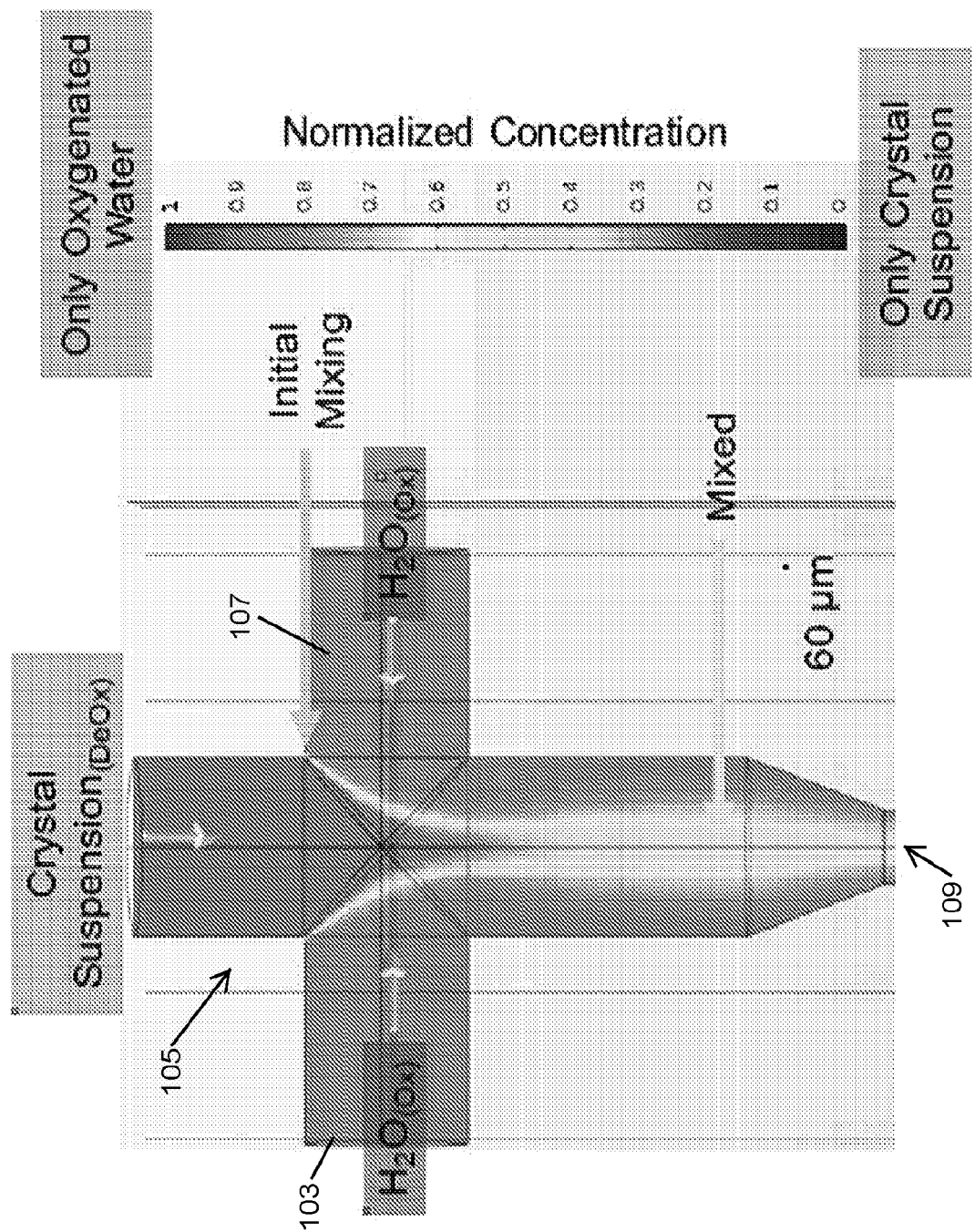
FIG. 2 is a schematic view of the mixer component of FIG. 1A generating a mixture of a crystal suspension and oxygenated water.

The schematic illustration of FIG. 2 is color coded to graphically demonstrate dissolved oxygen diffusion into a deoxygenated aqueous crystal suspension containing 10 μm crystals via hydrodynamic focusing. In the example of FIG. 2, two of the input channels 103, 107 are coupled to an oxygenated water source (i.e., pump, regulator, etc.) while the third input channel 105 is coupled to a crystal suspension source. The schematic illustration of FIG. 2 is color coded to graphically demonstrate the normalized concentration of the mixture at various locations within the mixer ranging from portions containing only crystal suspension to portions containing only oxygenated water.

In the example of FIG. 2, a mixer component was used during SLAC beam time and run continuously during at least two shifts of 12 hours each. Mixing times of a few milliseconds were intended and reaction times of several seconds were probed. The output channel 109 of the mixer was coupled to a gas dynamic virtual nozzle (GDVN) through one 30 cm capillary with a 50 μm ID and a second 50 cm long capillary in series. The flow rate of the oxygenated water in input channels 103, 107 was 16 μL per minute. The flow rate of deoxygenated water (i.e., the crystal suspension) in input channel 105 was 8 μL per minute. The flow rate of the mixture through the output channel 109 was 40 μL per minute. The mixing time was 6 ms and the mixing distance was 300 μm. The reaction time probed was 6 s.

Figure 3:
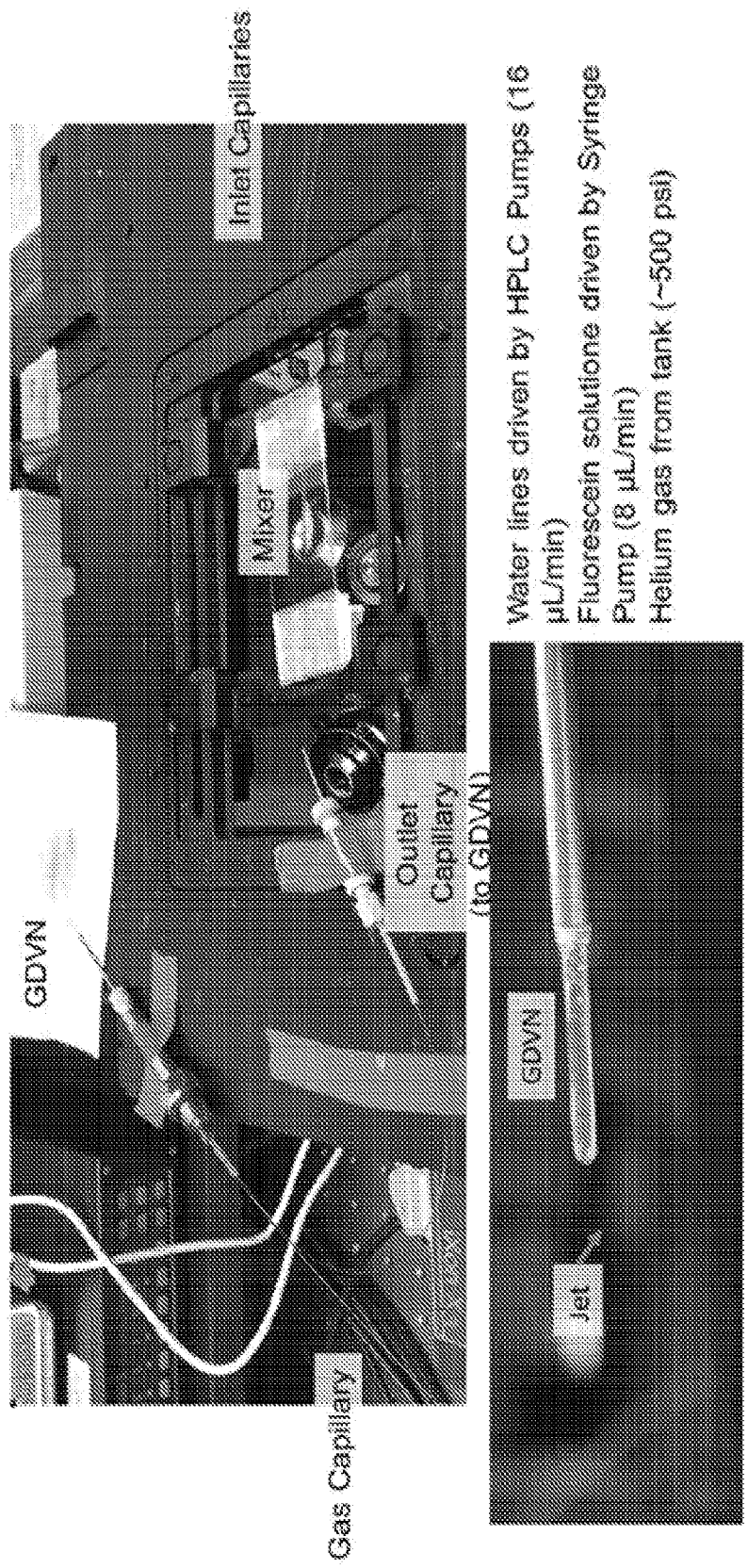
FIG. 3 is an example setup for use of the 3D printed mixer of FIG. 1A coupled to a gas dynamic virtual nozzle (GDVN).

FIG. 3 further illustrates various components of another experimental setup that utilizes the mixer component of FIG. 1A. Inlet capillaries are coupled to the input channels 103, 105, 107 and an outlet capillary coupled the output channel 109 of the mixer to a gas dynamic virtual nozzle (GDVN). The GDVN produces a jet expelling the mixture from the mixer component. In the example of FIG. 3, water lines were driven by HPLC pumps at 16 μL per minute, a fluorescein solution was driven by syringe pump at 8 μL per minute, and helium gas was introduced from a tank at approximately 500 psi through a gas capillary to the GDVN.

Figure 4:
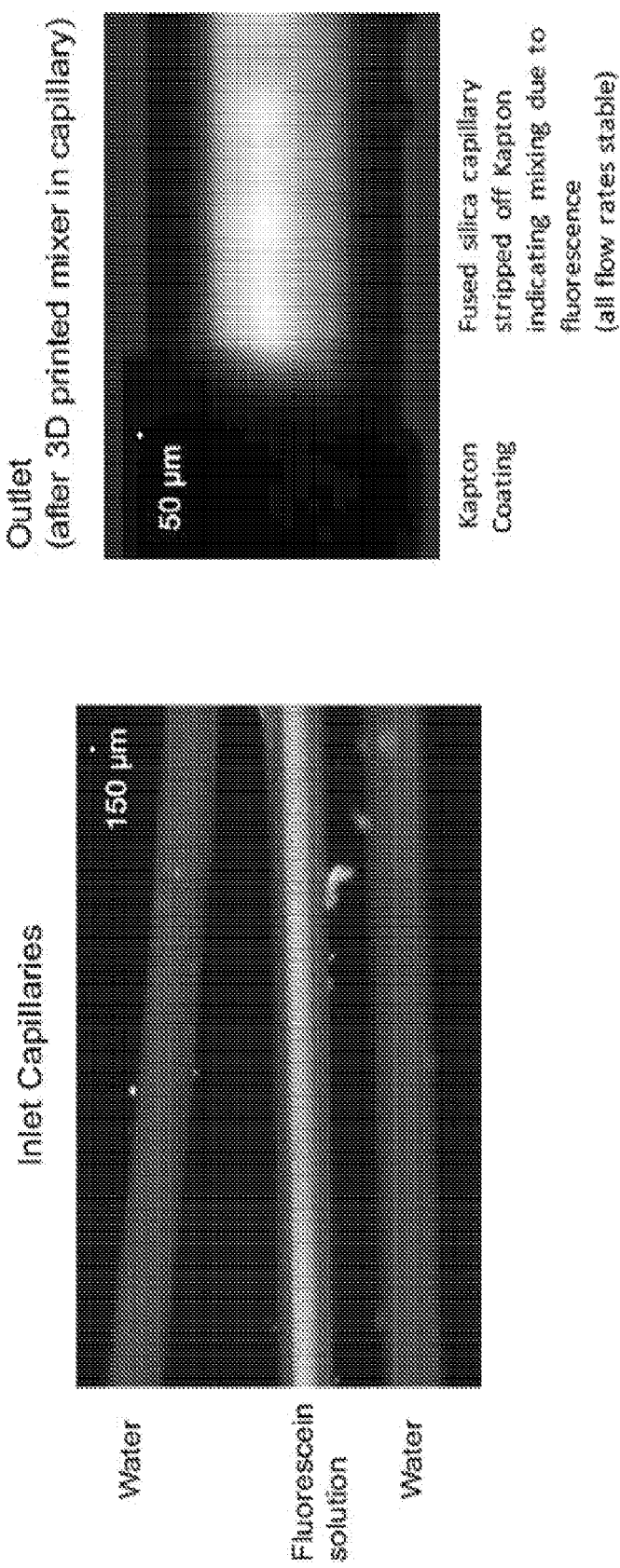
FIG. 4 is a series of images showing a fluorescein solution mixing with water using the mixer component of FIG. 1A.

FIG. 4 illustrates the fluids moving through the internal channels of the mixer component of FIG. 1A during operation of the experimental set up of FIG. 3. The image on the left of FIG. 4 shows the inlet capillaries at a scale of 150 μm and shows water moving through two inlet capillaries while the fluorescein solution moves through the third inlet capillary. The image on the right of FIG. 4 shows, at a scale of 50 μm, the outlet capillary after the water and fluorescein solution are mixed by the mixer component. In the example of FIG. 4, a Kapton coating is used to demonstrate fused silica of the capillary stripped off indicating mixing due to fluorescence.

Figure 5A:
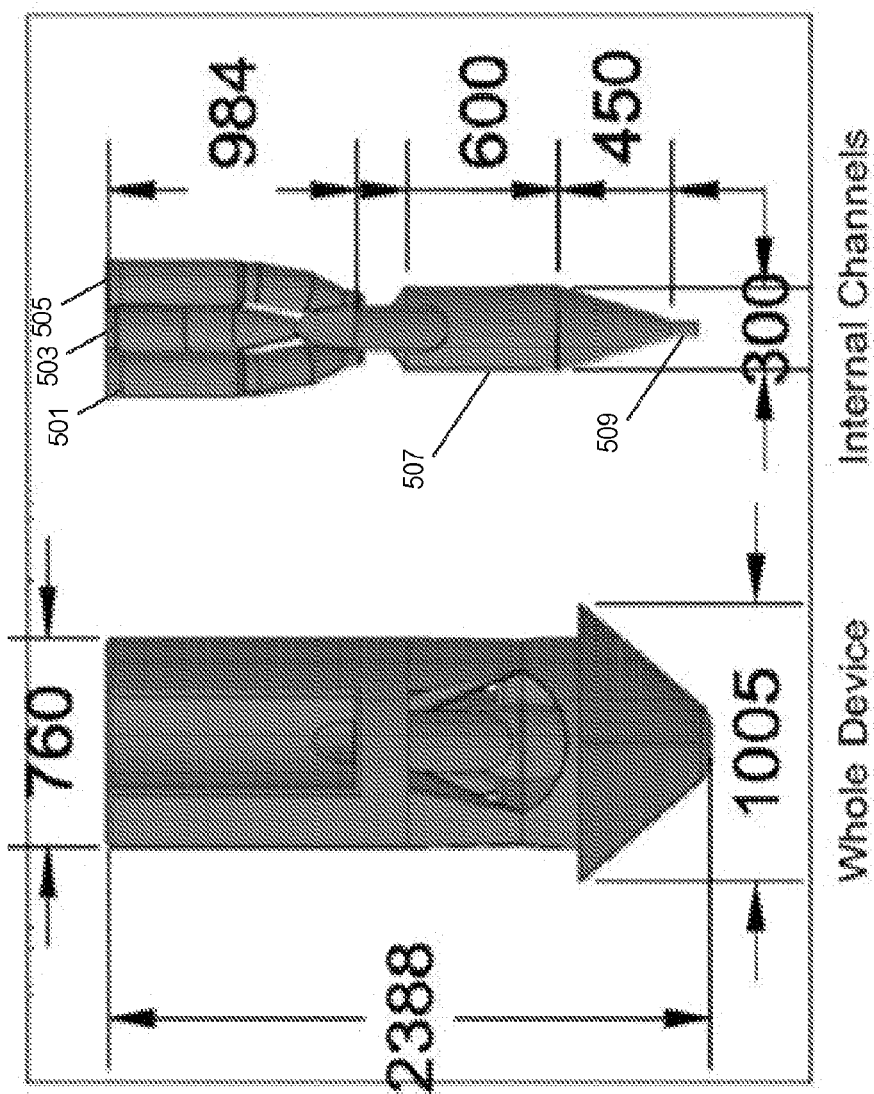
FIG. 5A is a top view of an exterior and the interior channels of a component piece including both a mixer and a nozzle in accordance with one embodiment.
Figure 5B:
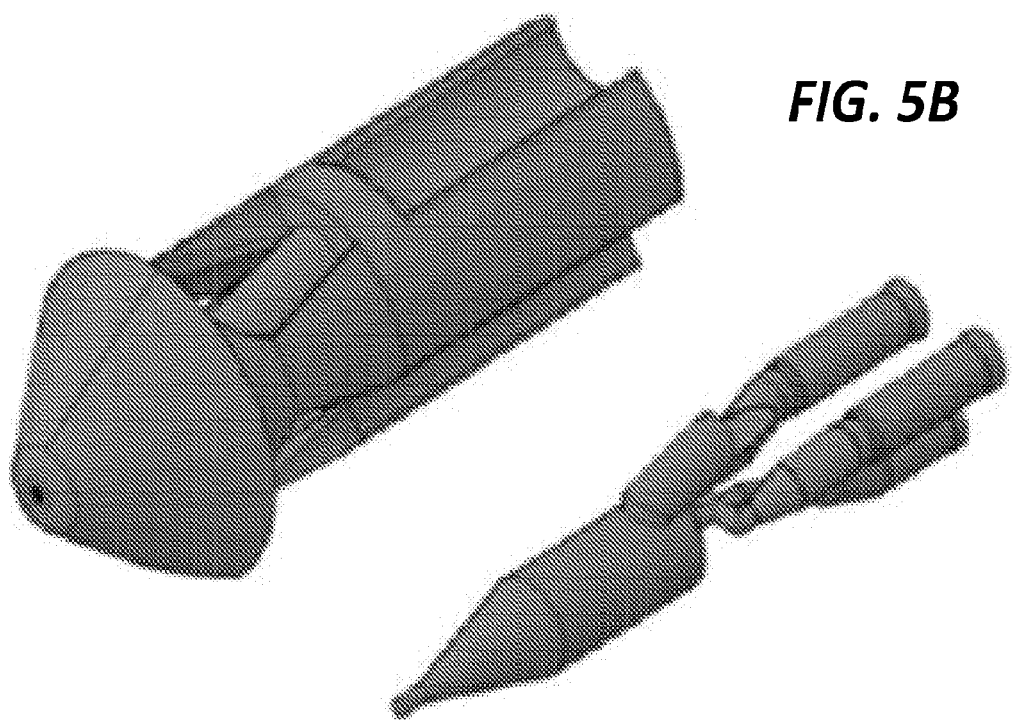
FIG. 5B is a perspective view of the exterior and the interior channels of the component piece of FIG. 5A.
Figure 5C:
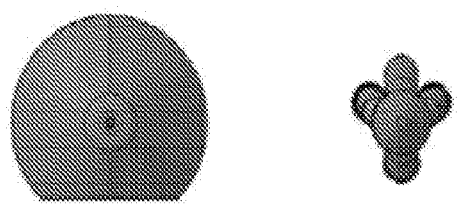
FIG. 5C is a front view of the exterior and the interior channels of the component piece of FIG. 5A.
Figure 5D:
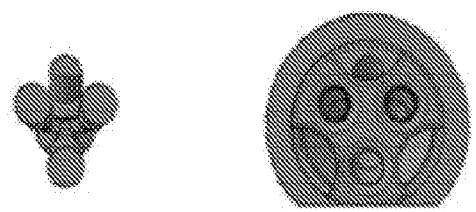
FIG. 5D is a rear view of the exterior and the interior channels of the component piece of FIG. 5A.

In the examples illustrated above, the 3D printed piece includes a mixer that is coupled to a separate GDVN by capillary tubing. In those examples, the output fluid jet is produced through the GDVN. However, in other examples, a fluid jet is integrated directly into the same 3D printed component piece as the mixer. FIGS. 5A-5D illustrate one example of such a hybrid mixer/nozzle component. FIG. 5A shows a top view of the hybrid mixer/nozzle component. The exterior of the component is shown in the image on the left side of FIG. 5A and the internal channels are shown in the image on the right side of FIG. 5A. Dimensions of the component exterior and internal channels are shown in FIG. 5A in micrometers. FIG. 5B shows the hybrid component of FIG. 5A in perspective view. The exterior is shown on the left side of FIG. 5B and the internal channels are shown on the right side of FIG. 5B. FIG. 5C illustrates a front view of the exterior of the hybrid component on the left and a front view of the internal channels of the hybrid component on the right. FIG. 5D illustrates a rear view of the exterior of the hybrid component on the right and a rear view of the internal channels of the hybrid component on the left.

Like in the mixer of FIG. 1A, the hybrid component of FIGS. 5A through 5D includes three input channels 501, 503, 505 that are all coupled to an output channel 507. However, the hybrid component of FIGS. 5A through 5D is also equipped with a nozzle 509 that expels the mixture as a fluid jet. In this example, the nozzle 509 is formed of the same piece of material as the input channels and the output channel as part of the 3D printing process.

Figure 6:
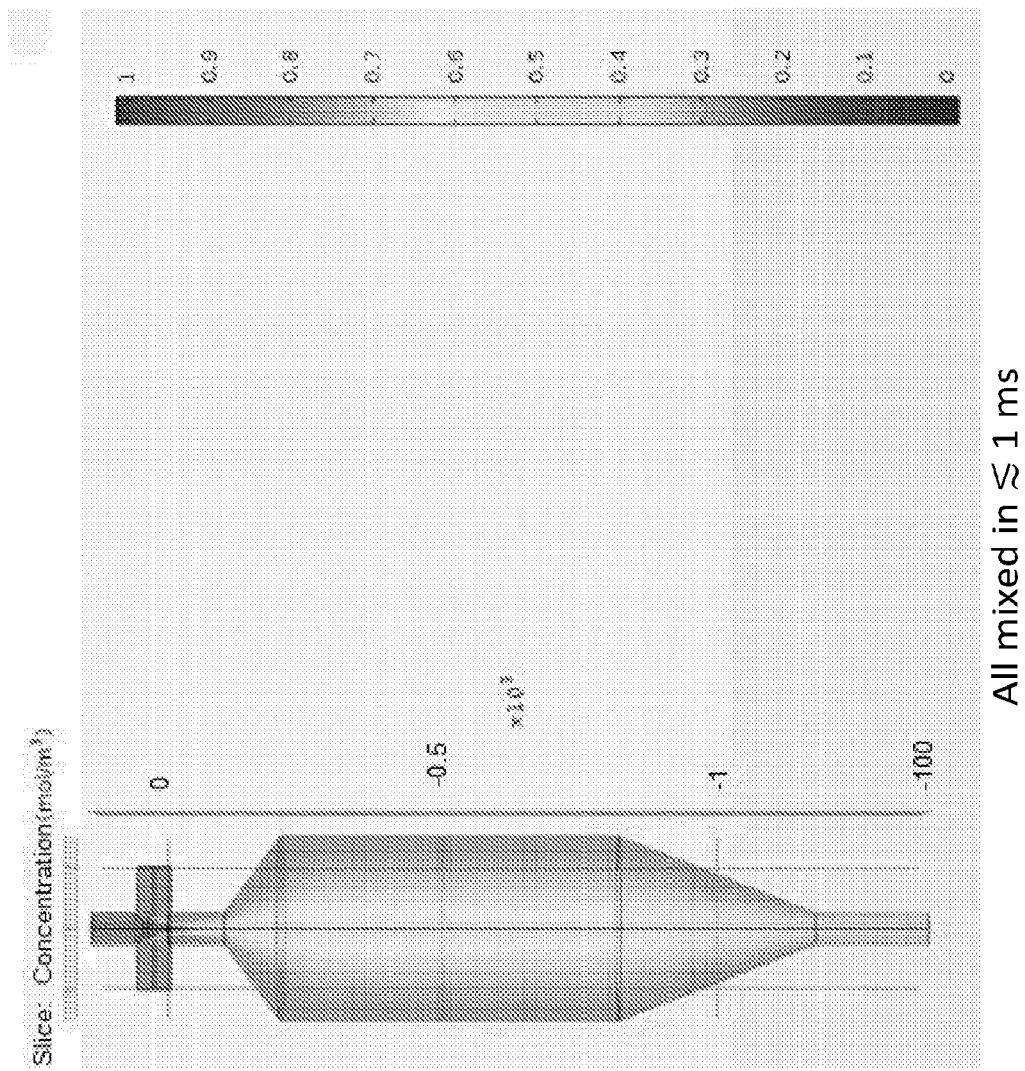
FIG. 6 is a schematic view of the component piece of FIG. 5A generating a mixture of a crystal suspension and oxygenated water.

FIG. 6 schematically illustrates relative concentrations of the mixture in the output channel 509 of the hybrid component based on numerical modeling of conviction and diffusion. FIG. 7 illustrates the flow rates of the crystal suspension and the substrate flow rate of each inlet at various time points during an experimental mixing process.

Figure 8:
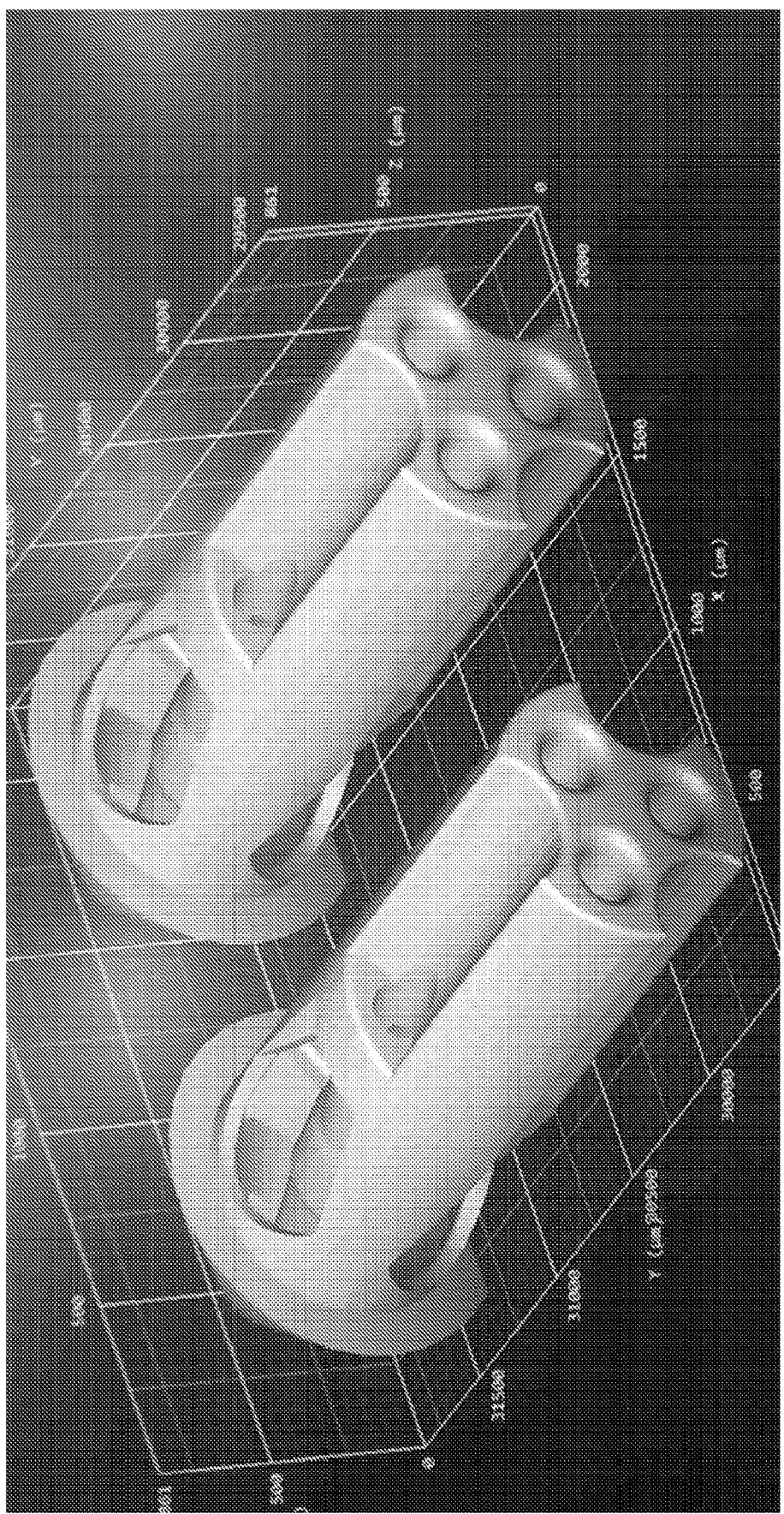
FIG. 8 is a perspective view of a CAD drawing for creating the component piece of FIG. 5A using 3D printing technology.
Figure 9:
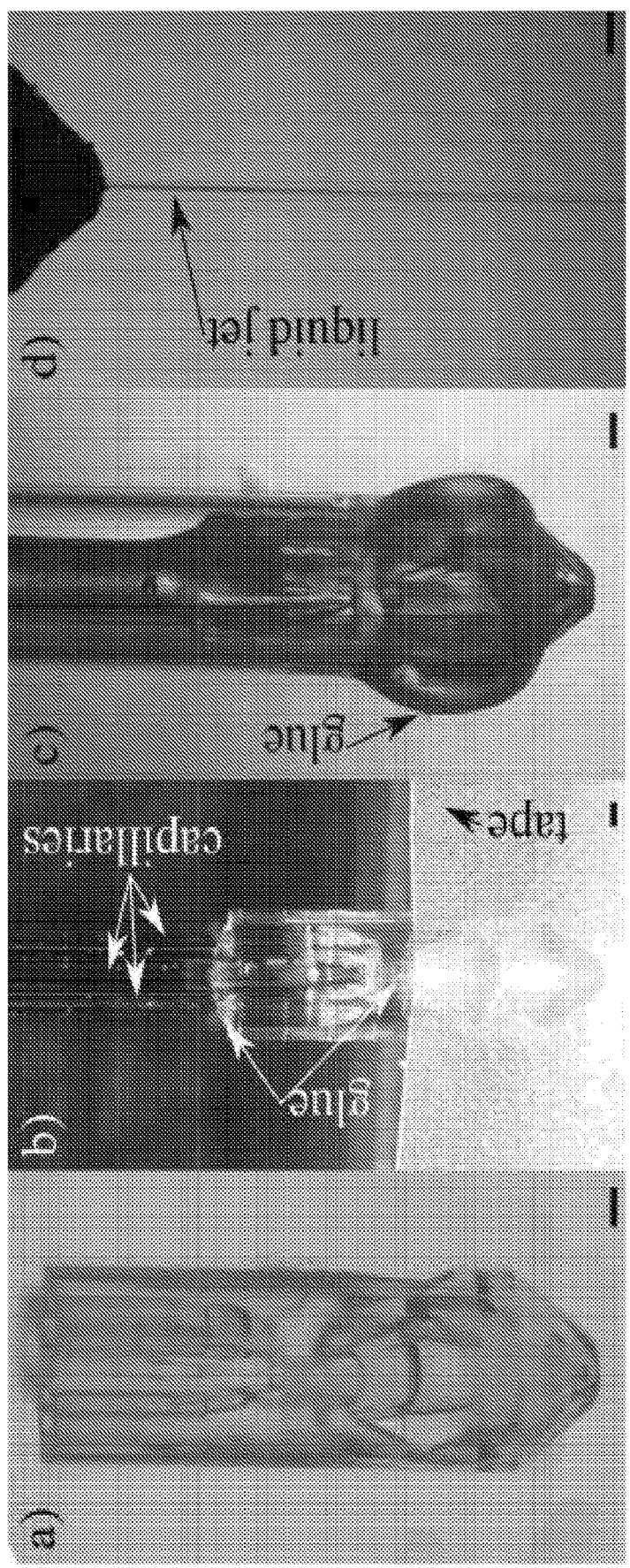
FIG. 9 and FIG. 10 are bright field image views of the component piece of FIG. 5A created using 3D printing technology according to the CAD drawing of FIG. 8.
Figure 10:
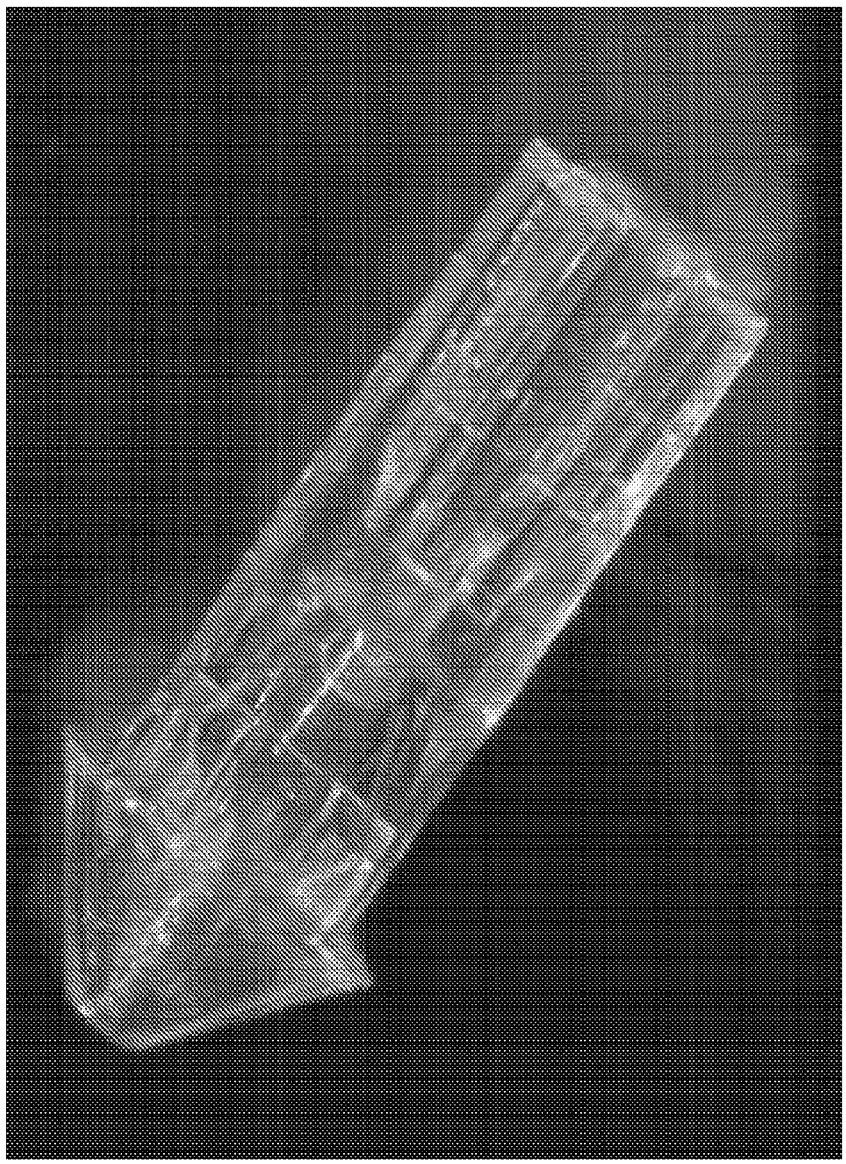
Figure 12:
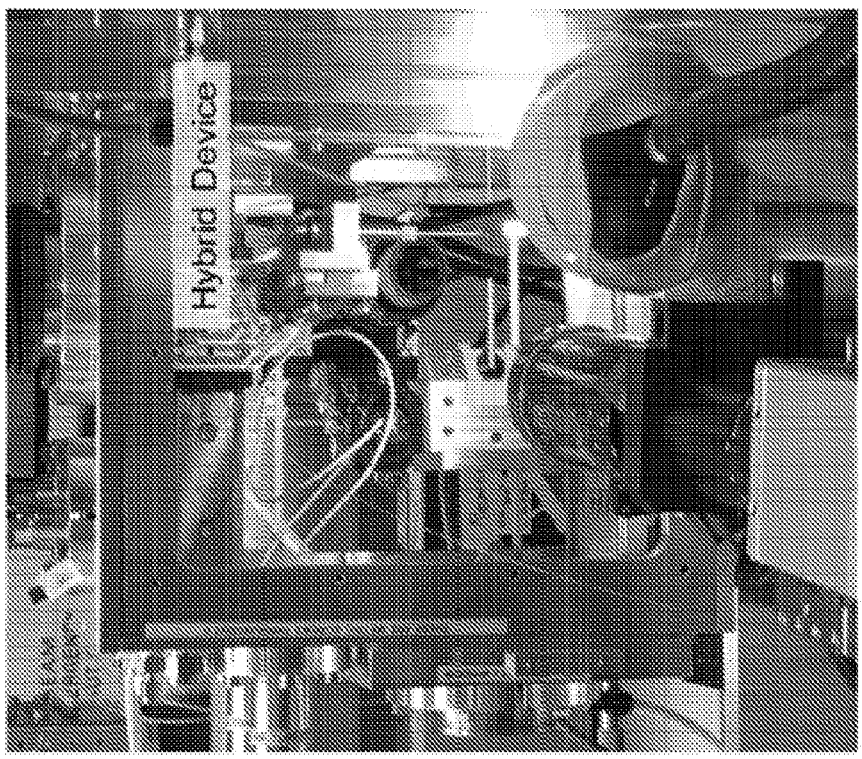
FIG. 12 is a perspective view of an experimental setup using the component piece of FIG. 5A.
Figure 11:
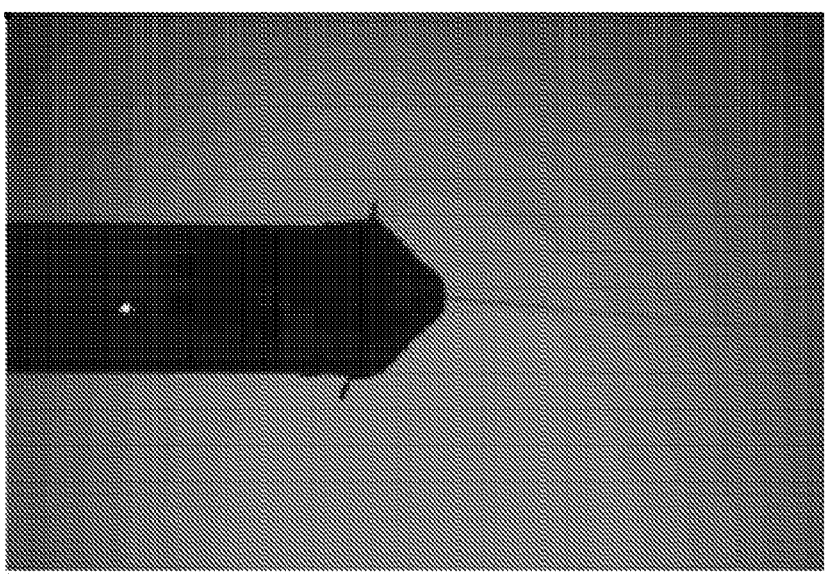
FIG. 11 is a side view of a water jet emitted from the component piece of FIG. 5A.

As discussed above, a mixer component (such as illustrated in FIGS. 1A-1C) or a hybrid mixer/nozzle component (such as illustrated in FIGS. 5A-5D) can be produced as a single piece using 3D printing technology. FIG. 8 illustrates an example of a CAD drawing of the hybrid component of FIGS. 5A-5D that can be used by a 3D printing system to create the hybrid component. FIGS. 9 and 10 are bright field images of the 3D printed hybrid component created using the CAD drawing of FIG. 8. FIG. 11 illustrates a water jet expelled from the hybrid component and FIG. 12 illustrates an example of an experimental set up using the 3D printed hybrid component.

Figure 13A:
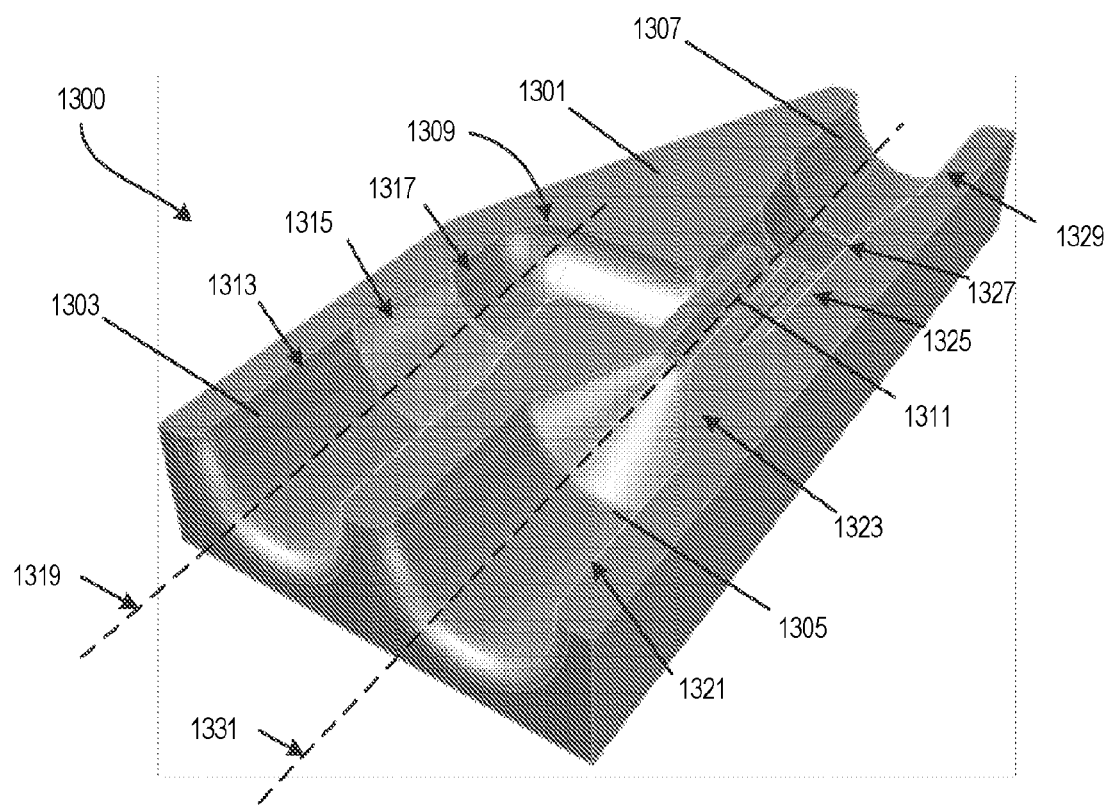
FIG. 13A is a cut-away perspective view of a coaxial mixer according to another embodiment.
Figure 13B:
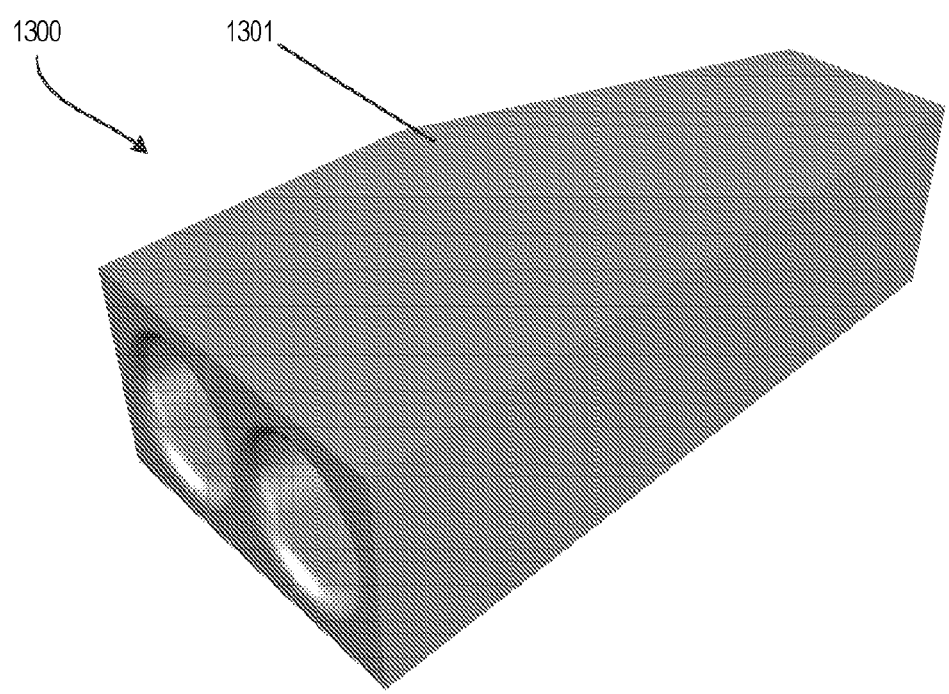
FIG. 13B is a perspective view of the coaxial mixer of FIG. 13A.

FIGS. 13A and 13B illustrate another example of a microfluidic mixer. In this example, the outputs of two fluid channels are arranged so that fluid from one channel is added coaxially into the output stream from the other channel. The microfluidic mixer 1300 includes a 3D printed housing component 1301 with a first fluid inlet channel 1303 and a second fluid inlet channel 1305 formed internally. The first fluid inlet channel 1303 and the second fluid inlet channel 1305 merge into an outlet channel 1307. The terminal end 1309 of the first fluid inlet channel 1303 forms two angles and empties into the outlet channel 1307. The terminal end 1311 of the second fluid inlet channel 1305 empties directly into the outlet channel 1307 and is arranged coaxial with a portion of the terminal end 1309 of the first fluid inlet channel 1303 where the first fluid inlet channel 1305 empties into the outlet channel 1307. As a result, fluid from the second fluid inlet channel 1305 is introduced into the outlet channel 1307 coaxially in the middle of the stream of fluid flowing into the outlet channel 1307 from the first fluid inlet channel.

With continued reference to FIG. 13A, the first fluid inlet channel 1303 includes a first portion 1313 having a first diameter (e.g., about 360 μm-380 μm), a second portion 1315 having a second diameter that is variable and gradually reduced (e.g., funnel-shaped) to be smaller than the first diameter, and a third portion 1317 having a third diameter (e.g., about 100 μm-150 μm) that is smaller than the first diameter and the second diameter. The third portion 1317 merges into the terminal end 1309. The first fluid inlet channel 1303 defines a central axis 1319. The terminal end 1309 receives the fluid from the first fluid inlet channel 1303 and transports the fluid in a transverse direction to the central axis 1319 and then in a direction parallel to the central axis 1319 and into the outlet channel 1307. In one construction, the transverse direction may be perpendicular, for example at a 90° angle relative to the central axis 1319.

The second fluid inlet channel 1305 includes a fourth portion 1321 having a fourth diameter (e.g., about 360 μm-380 μm) and a fifth portion 1323 having a fifth diameter that is variable and is gradually reduced (e.g., funnel-shaped), which merges into the terminal end 1311. The terminal end 1311 extends for a pre-determined distance. The terminal end 1311 includes a sixth portion having a sixth diameter less than the fourth diameter. The outlet channel 1307 includes a seventh portion 1325 having a seventh diameter (e.g., 50-100 μm), an eighth portion 1327 having an eighth diameter that is variable and gradually increases, and a ninth portion 1329 having a ninth diameter (e.g., 50-100 μm) greater than the seventh diameter. The seventh diameter and the ninth diameter could be equal.

The second fluid inlet channel 1305 defines a central axis 1331. The terminal end 1311 receives the fluid from the second fluid inlet channel 1305 and transports the fluid coaxially along the central axis 1331 and into the outlet channel 1307. The central axis 1331 is oriented parallel with the central axis 1319.

Figure 13C:
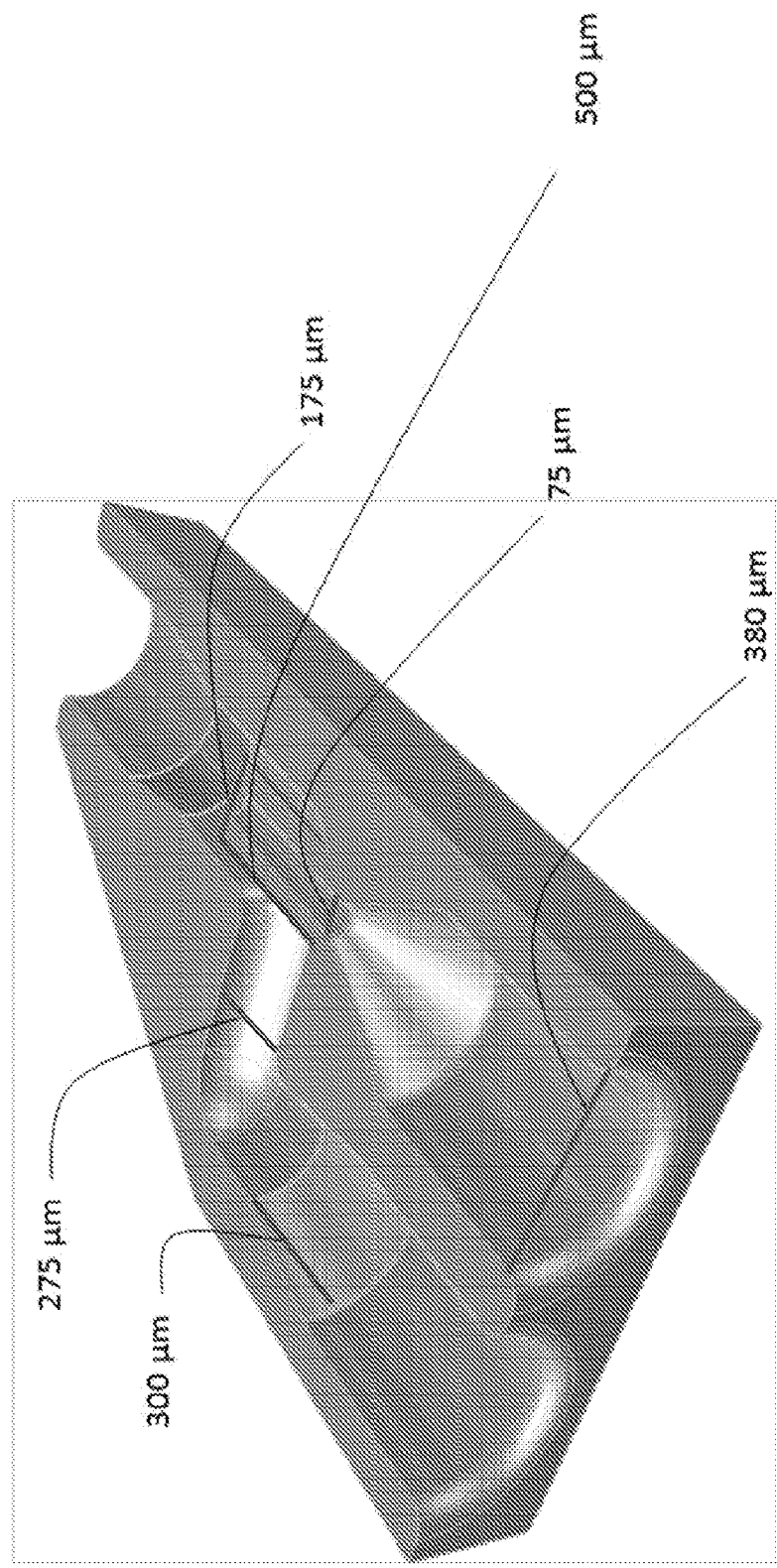
FIG. 13C is the cut-away perspective view of FIG. 13A illustrating the internal dimensions of the internal fluidic channels.

FIG. 13C and the tables of FIG. 14 illustrate the dimensions of the microfluidic mixer 1300 in this specific example. However, in other implementations, the specific measurements, dimensions, and layout may be different. In the example of FIGS. 13A, 13B, and 13C, both the first fluid inlet channel 1303 and the second fluid inlet channel 1305 have a diameter of 380 µm. The internal diameter of the terminal end 1309 of the first fluid inlet channel 1303 is 275 µm while the internal diameter of the terminal end 1311 of the second fluid inlet channel 1305 is 75 µm. The diameter of the first fluid inlet channel 1303 and the diameter of the second fluid inlet channel 1305 each tapers down to the diameter of its respective terminal end 1309, 1311 along a length of 300 µm. The terminal end 1311 of the second fluid inlet channel 1305 extends into the terminal end 1309 of the first fluid inlet channel 1303 with an exterior length of 500 µm and an exterior diameter of 175 µm. It is noted that in general, the largest channels are the capillary inlets (e.g., the first fluid inlet channel 1303 and the second fluid inlet channel 1305), which are typically 360 µm. The other dimensions of the inlet and outlet channels and terminal ends can be adjusted by the needs of the experiment in terms of mixing times and crystal size, flow rates etc. The availability of the 3D printing method is very versatile and allows for alternative sizes and design options.

The microfluidic mixer 1300 of FIGS. 13A, 13B, and 13C can be used to mix various types of fluids. For example, a crystal suspension can be mixed with a substrate solution by introducing the substrate solution through the first fluid inlet channel 1303 (e.g., as a "substrate channel") and introducing the crystal suspension through the second fluid inlet channel 1305 (e.g., as a "crystal channel"). The substrate solution may comprise a buffer with the substrate comprising a gas such as oxygen, a molecule serving as the substrate for an enzyme reaction, a protein complex dissociating or associating, and the like. A person of ordinary skill in the art would understand that this list provides only a few examples of the substrate solution, but there exists numerous options for the substrate solution not specifically listed herein.

Figure 15:
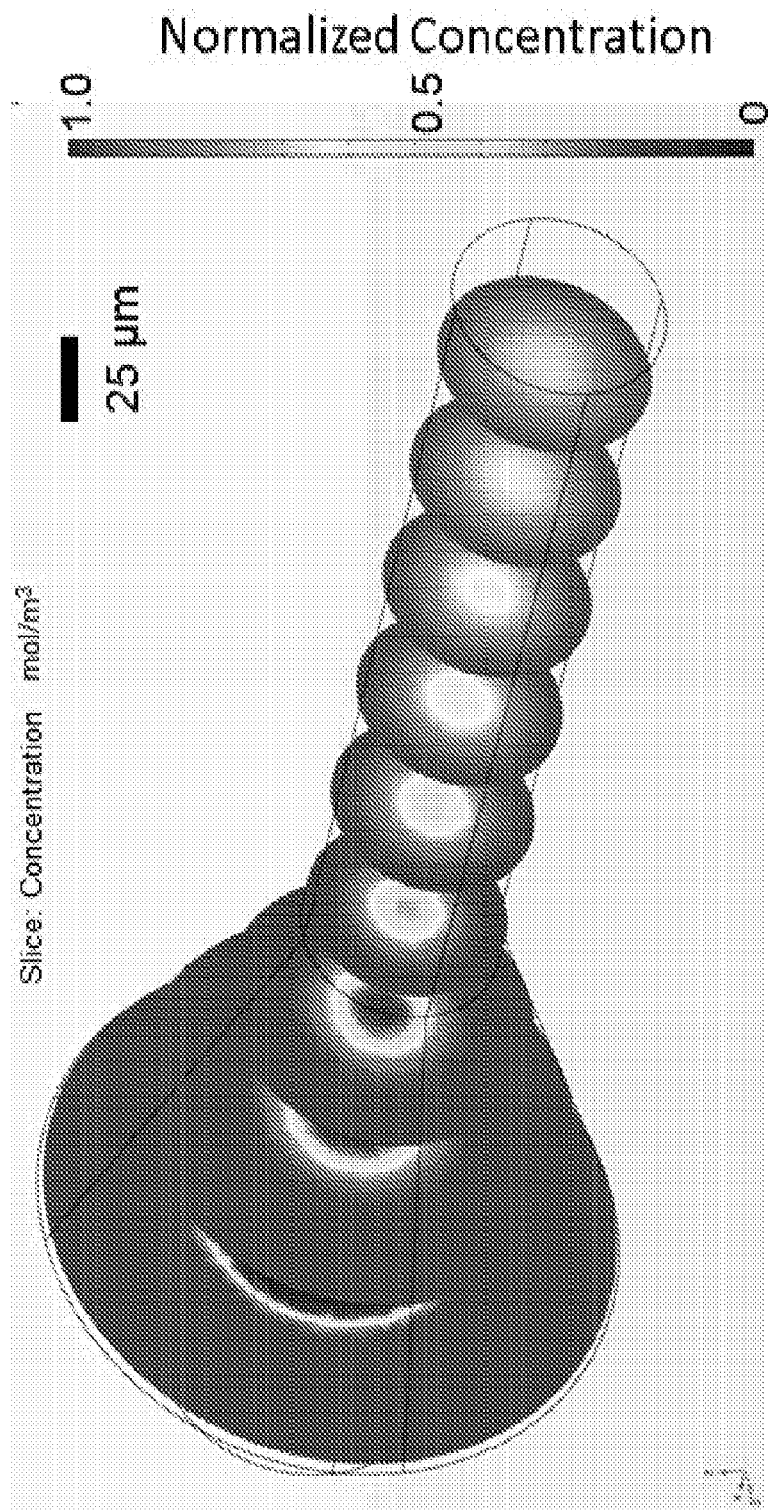
FIG. 15 is a graph of an example of relative concentrations mixed using the coaxial mixer of FIG. 13A.
Figure 16:
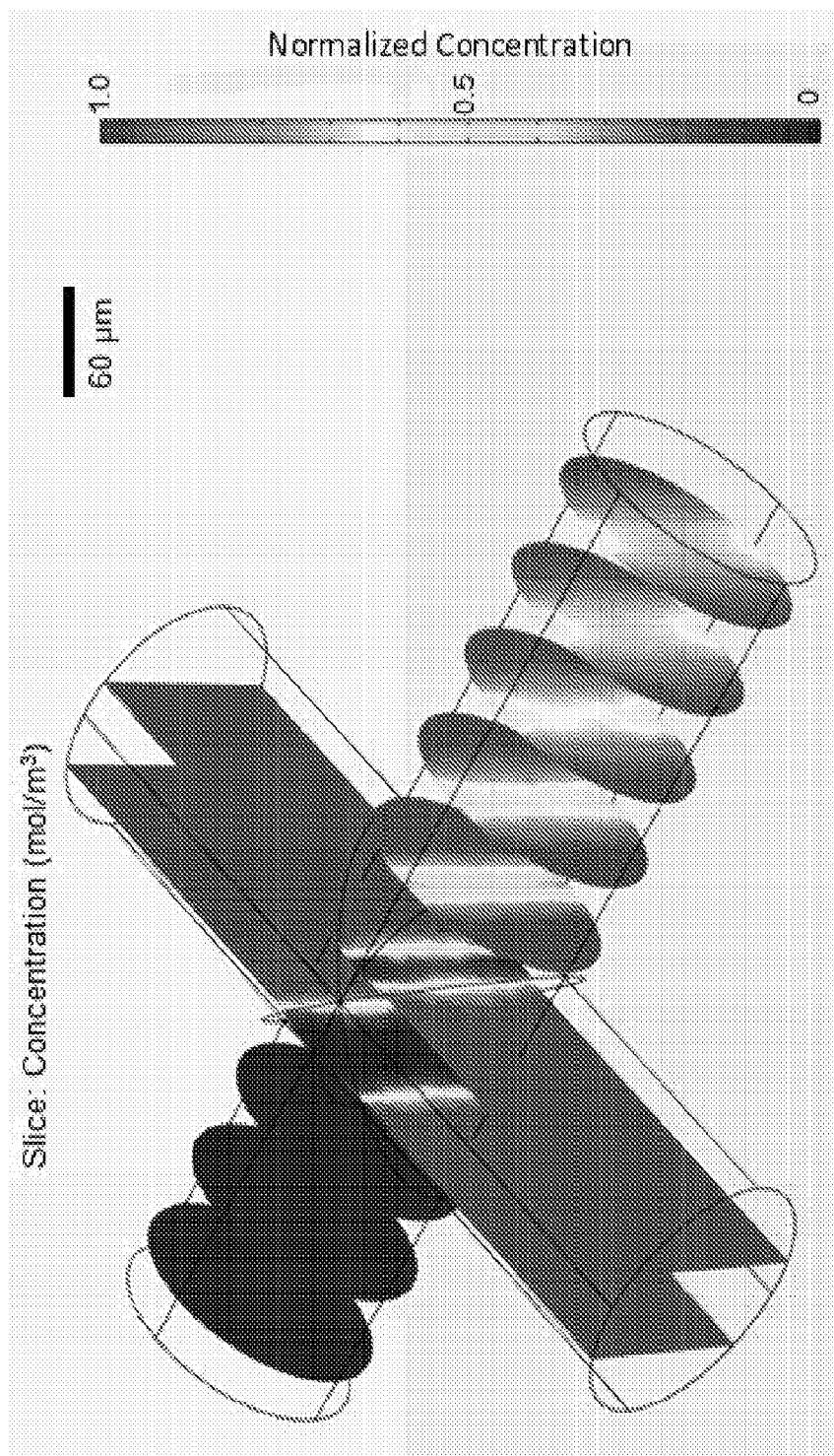
FIG. 16 is a graph of an example of relative concentrations mixed using the mixer of FIG. 1A.

The microfluidic mixer 1300 can effectively reduce mixing times for given flow rates and geometry. FIGS. 15 and 16 illustrate examples of the normalized concentrations of fluids mixed using the microfluidic mixer 1300 and the microfluidic mixer of FIGS. 1A-1C, respectively. In this example, the mixing time is reduced from 3 ms to 1 ms using the microfluidic mixer 1300.

Figure 17:
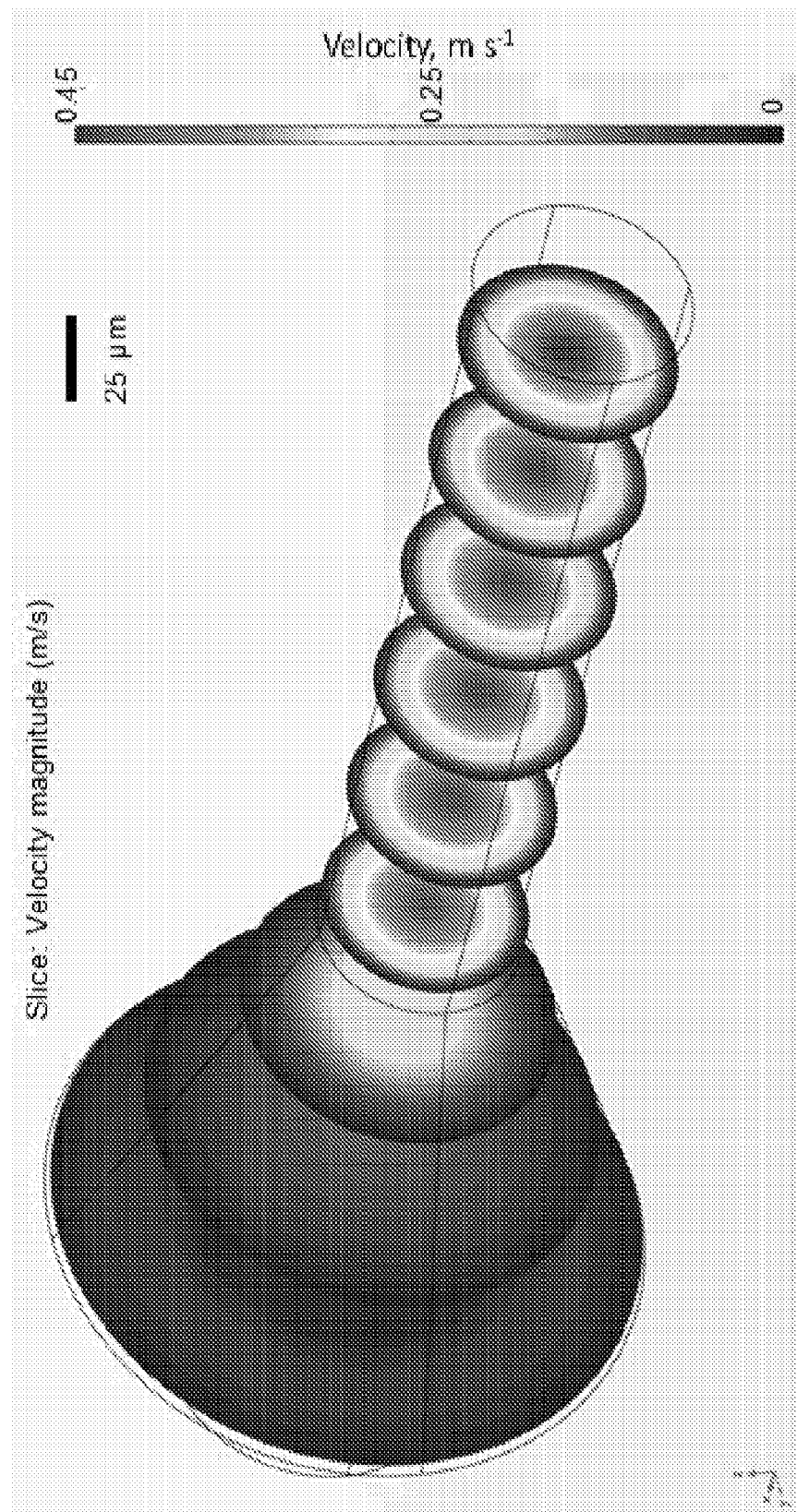
FIG. 17 is a graph of an example of relative velocity magnitudes using the mixer of FIG. 13A.
Figure 18:
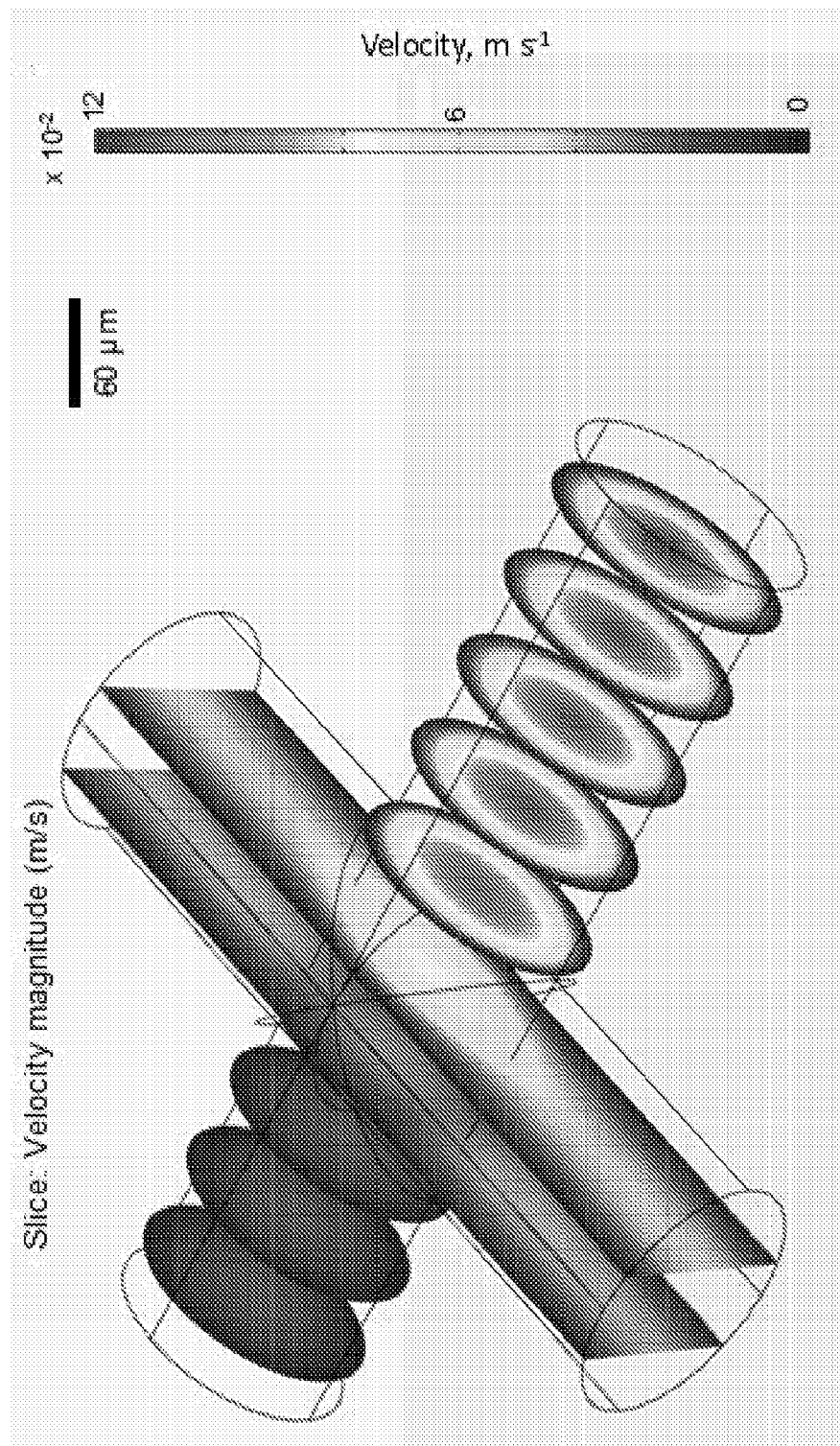
FIG. 18 is a graph of an example of relative velocity magnitudes using the mixer of FIG. 1A.

The microfluidic mixer 1300 also reduces variations in flow rate for crystals and thus also reduces variations in the time points probed with serial femtosecond crystallography (SFX). FIGS. 17 and 18 illustrate the velocity of materials moving through the device using the microfluidic mixer 1300 and the microfluidic mixer of FIGS. 1A-1C, respectively. In this example, crystals of a few µm$^3$ are injected in the middle of the microfluidic mixer and transported along the microfluidic mixer subsequent tubing (not shown) to the injector. The flow rates determine the achievable reaction time points. Assuming a length of 1 m of the connecting tubing (which, in some embodiments, would be an overestimation), the crystals stream would not be widened through diffusion. The variation in flow rate thus relates to the variations in flow rates the crystals would experience. In the coaxial design, the crystals are confined in the middle streaming through the mixer and experience about 10% variations in the velocity and, consequently, time points probed in a TR-SFX experiment. By comparison, in some examples of the microfluidic mixer of FIGS. 1A-1C, this variation may be as great as 100% since the crystals can spread out to the edges of the mixer walls.

Example

Performing experiments using TR-SFX at XFELs requires suitable sample delivery into the focus of the X-ray beam. Microfluidics is a suitable technique for this purpose using liquid jets in the form of Gas Dynamic Virtual Nozzles (GDVNs). Classical GDVNs are manufactured using glass capillaries or multilayer micro-fabricated elastomer devices requiring tedious manual assembly steps. Recent developments in two photon printing methods enable direct and repeated printing of GDVNs reducing the assembly time and demanding manual fabrication steps, facilitate prototyping and allow direct integration of additional microfluidic components, such as mixers. The latter is essential for TR-SFX of biological processes. Here, it is demonstrated a device combing a GDVN and a hydrodynamic mixer based on the diffusive mixing of a substrate with crystals in a thin stream of liquid, enabling fast and controlled mixing in less than 5 ms, with flow rates compatible with creating liquid jets using GDVNs. The approach facilitates the study of enzyme kinetics in which intermediate states occur in the order of 150 ms, and is fully compatible with the requirements of current SFX experimental set-ups at XFEL sources, both in Helium atmosphere as well as under vacuum. It is envisioned that these 3D-printed devices will become a versatile and robust tool in TR-SFX due to their ease of use and fabrication.

FIGS. 5A-D illustrate schematics of the device used in this experiment, combining a hydrodynamic mixer and the GDVN described by Nelson et al. The entire device is designed to fit inside a glass capillary with an inner diameter (ID) of 760 µm, enabling use of established nozzle rods. Designs are made using AutoCAD (Autodesk, USA) and converted using DeScribe software (Nanoscribe, Germany). Printing was performed using the Photonic Professional GT (Nanoscribe,) with IP-S resist (Nanoscribe). Developer (MicroChem, USA) was used in an ultrasonic bath to dissolve remaining resist in cycles of 15 minutes with subsequent immersion in isopropyl alcohol and evaluation of the developing process, requiring on average four cycles to remove all resist from the inner cavities. Different reaction time points may be reached by varying the flow rates and the channel geometry of the combined microfluidic device. FEM simulations were performed using COMSOL Multiphysics (COMSOL, USA) to predict necessary flow rates. The simulation was performed with viscosities matching aqueous crystal suspension and precipitant solution. The crystal size of the KDO8PS enzyme in the aqueous solution was measured and accordingly simulated with ~10 µm.

Applied flow velocities and resultant reaction time points are shown in FIG. 7. The mixing time was <5 ms for all flow rates simulated. An exemplary map of the concentration of precipitant inside the channels is depicted in FIG. 6. Crystal suspension is inserted inside the middle inlet and the precipitant equally on the sides. The simulated area comprises 100 µm from the inlets to the mixing region and the entire outlet channel from the mixing region to the outlet of the GDVN.

A device combining a hydrodynamic mixer and a GDVN, was successfully employed for forming liquid jets, usable for TR-SFX, at the Macromolecular Femtosecond Crystallography (MFX setup) at the Linac Coherent Light Source (LCLS). FIGS. 5A-D display the device CAD drawings and FIGS. 9A-D show the process from the 3D printed and developed (A) to the operated device at the MFX setup at LCLS (D). Additionally, the assembly steps to obtain a leakage free device are further shown. Glass capillaries are glued to the fluid inlets (FIG. 9B) followed by mounting inside a glass capillary for gas supply (FIG. 9C), as described in detail by Nelson et al. A stable liquid jet (FIG. 9D) was obtained both at in-house testing, and during operation at MFX. Flow rates were adjusted to generate a stable jet and to reach different reaction time points for TR-SFX with one device. According to simulations, time points ranging from 30 to 144 ms were reached with the presented device (FIG. 7). Further sample consumption and optimization of hit rates can be achieved by adjusting the flow rates.

The reproducible and robust fabrication of a combined microfluidic mixer and liquid jet device suitable for fast mixing and liquid jet injection for TR-SFX with XFELs has been demonstrated. Experiments can be conducted in air, helium or vacuum and enable crystallographic studies of enzyme kinetics of important processes including intermediate states on the ms time scale. The ease of use and fabrication of these devices will enable further sample systems to be investigated with TR-SFX leading to novel insights in protein dynamics.

Thus, the invention provides, among other things, a single-piece component for mixing fluids for use, for example, in crystallography. Various features and advantages of the invention are set forth in the accompanying drawings.

What is claimed is:

1. A system for conducting time-resolved serial femtosecond X-ray crystallography, the system comprising:
   a hybrid nozzle including a microfluidic mixer integrally formed with a liquid jet injector, the hybrid nozzle further including
      a housing;
      a first fluid inlet channel formed in the housing and configured to receive a substrate solution,
      a second fluid inlet channel formed in the housing and configured to receive a crystal suspension, and
      an outlet channel formed in the housing and coaxially formed with the second fluid inlet channel and in fluid communication with the first fluid inlet channel to provide mixing of the substrate solution and the crystal suspension within 1 ms to 5 ms, and
      wherein the mixture is transported to a chamber via the liquid jet injector for crystallographic analysis,
      wherein the first fluid inlet channel includes a first portion having a first diameter, a second portion having a second diameter less than the first diameter, and a third portion having a third diameter less than the first diameter and the second diameter.

2. The system of claim 1, wherein the outlet channel provides mixing of the substrate solution and the crystal suspension in less than 3 ms.

3. The system of claim 1, wherein the first fluid inlet channel includes a first terminal end that merges with the outlet channel and transports the substrate solution into the outlet channel.

4. The system of claim 3, wherein the first fluid inlet channel defines an axis, and wherein the first terminal end includes a portion that is transverse to the axis and a portion that is parallel to the axis.

5. The system of claim 1, wherein the second fluid inlet channel includes a fourth portion having a fourth diameter, and wherein the first diameter and the fourth diameter are the same.

6. The system of claim 1, wherein the second fluid inlet channel includes a fourth portion including a fourth diameter, a fifth portion including a gradually-reduced diameter that merges into a second terminal end.

7. The system of claim 6, wherein the second terminal end extends for a pre-determined distance, the second terminal end including a sixth portion having a sixth diameter that extends along the pre-determined distance.

8. The system of claim 7, wherein the second terminal end merges with the outlet channel, and wherein the terminal end transports the crystal suspension into a center of the outlet channel.

9. The system of claim 7, wherein the second terminal end merges with the outlet channel, and wherein the second terminal end transports the crystal suspension coaxially into a center of a stream of the substrate solution flowing from the first fluid inlet channel into the outlet channel.

10. The system of claim 1, wherein the first fluid inlet channel includes a first terminal end that merges with the outlet channel thereby generating a first stream to transport the substrate solution into the outlet channel, and wherein the second fluid inlet channel includes a second terminal end that merges with the outlet channel thereby generating a second stream to transport the crystal suspension into the outlet channel, and further wherein the second stream is central to and surrounded by the first stream.

11. The system of claim 10, wherein second stream defines a velocity, and wherein the velocity varies by 10% to 20% as the second stream traverses the outlet channel.

12. The system of claim 10, wherein second stream defines a velocity, and wherein the velocity varies by 10% or less as the second stream traverses the outlet channel.

13. The system of claim 10, wherein the second stream remains centrally within the outlet channel along a length of the outlet channel.

14. The system of claim 1, wherein the first fluid inlet channel includes
   a first portion having a first diameter,
   a second portion having a second diameter less than the first diameter,
   a third portion having a third diameter less than the first diameter and the second diameter, and
   a first terminal end,
wherein the second fluid inlet channel includes
   a fourth portion including a fourth diameter,
   a fifth portion including a gradually-reduced diameter, and
   a second terminal end,
wherein the outlet channel is configured to receive a first stream of the substrate solution exiting the first terminal end and a second stream of the crystal solution exiting the second terminal end, and
wherein the outlet channel includes
   a seventh portion having a seventh diameter,
   an eighth portion having an eighth diameter greater than the seventh diameter, and
   a ninth portion having a ninth diameter greater than the eighth diameter.

15. A system for conducting time-resolved serial femtosecond X-ray crystallography, the system comprising:
   a hybrid nozzle including a microfluidic mixer integrally formed with a liquid jet injector, the hybrid nozzle further including
      a housing;
      a first fluid inlet channel formed in the housing and configured to receive a substrate solution,
      a second fluid inlet channel formed in the housing and configured to receive a crystal suspension, and
      an outlet channel formed in the housing and coaxially formed with the second fluid inlet channel and in fluid communication with the first fluid inlet channel to provide mixing of the substrate solution and the crystal suspension within 1 ms to 5 ms, and wherein the mixture is transported to a chamber via the liquid jet injector for crystallographic analysis, and wherein the second fluid inlet channel includes a fourth portion including a fourth diameter, a fifth portion including a gradually-reduced diameter that merges into a second terminal end.

16. The system of claim 15, wherein the second terminal end extends for a pre-determined distance, the second terminal end including a sixth portion having a sixth diameter that extends along the pre-determined distance.

17. The system of claim 16, wherein the second terminal end merges with the outlet channel, and wherein the terminal end transports the crystal suspension into a center of the outlet channel.

18. The system of claim 16, wherein the second terminal end merges with the outlet channel, and wherein the second terminal end transports the crystal suspension coaxially into a center of a stream of the substrate solution flowing from the first fluid inlet channel into the outlet channel.

19. A system for conducting time-resolved serial femtosecond X-ray crystallography, the system comprising:
a hybrid nozzle including a microfluidic mixer integrally formed with a liquid jet injector, the hybrid nozzle further including
a housing;
a first fluid inlet channel formed in the housing and configured to receive a substrate solution,
a second fluid inlet channel formed in the housing and configured to receive a crystal suspension, and
an outlet channel formed in the housing and coaxially formed with the second fluid inlet channel and in fluid communication with the first fluid inlet channel to provide mixing of the substrate solution and the crystal suspension within 1 ms to 5 ms, and wherein the mixture is transported to a chamber via the liquid jet injector for crystallographic analysis,
wherein the first fluid inlet channel includes
a first portion having a first diameter,
a second portion having a second diameter less than the first diameter,
a third portion having a third diameter less than the first diameter and the second diameter, and
a first terminal end,
wherein the second fluid inlet channel includes
a fourth portion including a fourth diameter,
a fifth portion including a gradually-reduced diameter, and
a second terminal end,
wherein the outlet channel is configured to receive a first stream of the substrate solution exiting the first terminal end and a second stream of the crystal solution exiting the second terminal end, and
wherein the outlet channel includes
a seventh portion having a seventh diameter,
an eighth portion having an eighth diameter greater than the seventh diameter, and
a ninth portion having a ninth diameter greater than the eighth diameter.

* * * * *